US012616607B2

(12) United States Patent
Zhu

(10) Patent No.: US 12,616,607 B2
(45) Date of Patent: *May 5, 2026

(54) PORTABLE HAND WARMER CHARGING CASE AND HAND WARMER ASSEMBLY

(71) Applicant: Guangdong Aoyun Technology Co., Ltd., Huizhou (CN)

(72) Inventor: Xueping Zhu, Huizhou (CN)

(73) Assignee: Guangdong Aoyun Technology Co., Latd., Huizhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/279,069

(22) Filed: Jul. 24, 2025

(65) Prior Publication Data

US 2025/0345203 A1      Nov. 13, 2025

Related U.S. Application Data

(63) Continuation-in-part of application No. 19/089,189, filed on Mar. 25, 2025, now Pat. No. 12,451,710.

(30) Foreign Application Priority Data

| | | |
|---|---|---|
| Jul. 9, 2024 | (CN) | .......................... 202421622634.6 |
| Mar. 19, 2025 | (CN) | .......................... 202520496218.4 |
| Jul. 15, 2025 | (CN) | .......................... 202521483945.3 |

(51) Int. Cl.
*A61F 7/00* (2006.01)
*H02J 7/00* (2006.01)
(Continued)

(52) U.S. Cl.
CPC ............ *A61F 7/007* (2013.01); *H02J 7/0013* (2013.01); *H02J 7/0044* (2013.01); *H02J 7/0049* (2020.01);
(Continued)

(58) Field of Classification Search
CPC ...................................................... A61F 7/007
See application file for complete search history.

(56) References Cited

U.S. PATENT DOCUMENTS

| | | | | |
|---|---|---|---|---|
| 2008/0053979 A1* | 3/2008 | Toya | .................. | A61H 23/0263 |
| | | | | 219/385 |
| 2016/0360350 A1* | 12/2016 | Watson | .................. | H04W 4/70 |

(Continued)

OTHER PUBLICATIONS 3-in-1 Electric Hand Warmers Rechargeable 2 Pack, 14000mAh Portable Dual-Sided Handwarmer with Charging Case, 3 Levels Fast Heating Pocket Warmers, Gifts for Men, Women, Raynauds, Hunting Gear, Amazon.com, Aug. 1, 2024, Innopower US, https://www.amazon.com/dp/B0DBTB8TKG?th=1.

*Primary Examiner* — Kaitlyn E Smith
(74) *Attorney, Agent, or Firm* — Hemisphere Law, PLLC

(57) ABSTRACT

A portable hand warmer charging case includes a case body. A placement chamber configured to place a hand warmer unit for charging is provided on the case body. The case body is provided with a first circuit board, a first charging unit, and a first battery. The first battery and the first charging unit are electrically connected to the first circuit board. When the hand warmer unit is placed in the placement chamber, the first circuit board is configured to output electrical energy, which is output by the first battery, from the first charging unit; and the first charging unit is configured to be adapted to a second charging unit on the hand warmer unit for use and transmit the electrical energy output by the first circuit board to the second charging unit on the hand warmer unit.

12 Claims, 32 Drawing Sheets

(51) Int. Cl.

| | |
|---|---|
| *H02J 7/34* | (2006.01) |
| *H02J 50/10* | (2016.01) |
| *H05B 3/06* | (2006.01) |

(52) U.S. Cl.

CPC .............. *H02J 7/342* (2020.01); *H02J 50/10* (2016.02); *H05B 3/06* (2013.01); *A61F 2007/0036* (2013.01); *A61F 2007/008* (2013.01)

(56) References Cited

U.S. PATENT DOCUMENTS

| | | | |
|---|---|---|---|
| 2022/0014031 A1* | 1/2022 | Thomas | ................ G06F 11/325 |
| 2025/0015618 A1 | 1/2025 | Du | |
| 2025/0133633 A1 | 4/2025 | Zhu | |
| 2025/0226678 A1 | 7/2025 | Zhu | |

* cited by examiner

PORTABLE HAND WARMER CHARGING CASE AND HAND WARMER ASSEMBLY

CROSS-REFERENCE TO RELATED APPLICATIONS

The application is a Continuation-in-Part of the U.S. application Ser. No. 19/089,189 filed on Mar. 25, 2025, and entitled "PORTABLE HAND WARMER CHARGING CASE AND HAND WARMER ASSEMBLY", which claims priority of Chinese patent application CN202520496218.4, filed on Mar. 19, 2025, and claims priority of Chinese Patent Application No. CN2025214839453, filed on Jul. 15, 2025, the entire disclosures of which are incorporated herein by reference.

TECHNICAL FIELD

The present disclosure relates to the technical field of hand warmers, and in particular, to a portable hand warmer charging case and a hand warmer assembly.

BACKGROUND

Whether it is double-sided or single-sided, existing hand warmers on the market are usually only able to warm one hand or one body part, making it difficult to simultaneously warm both hands or multiple body parts. Especially when a user needs to perform different actions with the hands separately or when a user intends to use the hand warmer to warm multiple body parts, it is hard for the current hand warmers to meet the need of the user. Furthermore, to charge an existing hand warmer, the existing hand warmer needs to be connected to an external power supply through a power cable. However, when people go out, especially at outdoors, it is difficult to find a power supply to charge the hand warmers. Therefore, there is an urgent need on the market for a charging case that is convenient to carry and can charge a hand warmer.

SUMMARY

The present disclosure aims to provide a portable hand warmer charging case and a hand warmer assembly. The problem of inconvenience of charging of the existing hand warmer unit at outdoors is solved.

In order to solve the technical problem, the technical scheme provided by the present disclosure is as follows.

A portable hand warmer charging case includes a case body, wherein a placement chamber configured to place a hand warmer unit for charging is provided on the case body; the case body is provided with a first circuit board, a first charging unit, and a first battery; the first battery and the first charging unit are electrically connected to the first circuit board; when the hand warmer unit is placed in the placement chamber, the first circuit board is configured to output electrical energy, which is output by the first battery, from the first charging unit; and the first charging unit is configured to be adapted to a second charging unit on the hand warmer unit for use and transmit the electrical energy output by the first circuit board to the second charging unit on the hand warmer unit.

Further, the first charging unit is a conductive probe, and the conductive probe is arranged at a bottom of the placement chamber.

Further, the first circuit board is located at the bottom of the placement chamber, and the first battery is located behind the case body.

Further, the first circuit board is provided with an indicator lamp unit configured to indicate a battery level state of the first battery and/or a charging state of the hand warmer unit.

Further, the indicator lamp unit includes a plurality of light-emitting bodies arranged on the first circuit board, and the plurality of light-emitting bodies are arranged side by side; the case body is further provided with a light guide hood; the light guide hood is provided with an accommodating slot at a position corresponding to each light-emitting body; the light-emitting body is located in the accommodating slot; a first light guide hole that is communicated with the accommodating slots is provided on the light guide hood; and a second light guide hole is provided at a position, corresponding to the first light guide hole, on the case body.

Further, the indicator lamp unit includes a battery level indicator lamp and a charging state indicator lamp, and the charging state indicator lamp is located next to the battery level indicator lamp.

Further, the first circuit board is provided with a function button; the case body is provided with a pressing member connected to the function button; and when the function button is operated, the first circuit board outputs electrical energy to the first charging unit.

Further, a first charging interface is provided on the first circuit board; and a first avoidance hole configured to avoid the first charging interface is provided on the case body.

Further, the indicator lamp unit, the function button, and first charging interface are arranged side by side in a thickness direction of the charging case; and the function button is located between the indicator lamp unit and the first charging interface.

Further, the case body includes a main body and a cover body connected to the main body to form the placement chamber; and the first circuit board, the first battery, the pressing member, the first avoidance hole, and the second light guide hole are all located on the main body.

Further, the placement chamber includes a first placement slot; the conductive probe is arranged at a bottom of the first placement slot; the main body includes a first outer cover and a first inner shell connected to the first outer cover to form the first placement slot, a first mounting chamber, and a second mounting chamber; the first inner shell is located on an inner side of the first outer cover; the first mounting chamber is located below the first placement slot; the first circuit board is arranged in the first mounting chamber; the first battery is arranged in the second mounting chamber; the second mounting chamber is located behind the first placement slot; and the pressing member, the first avoidance hole, and the second light guide hole are all located on the first outer cover.

Further, the cover body is rotatably connected to the main body; the placement chamber includes a second placement slot; the cover body includes a second outer cover and a second inner shell connected to the second outer cover to form the second placement slot; the second inner shell is at least partially located on an inner side of the second outer cover; a bottom of the second outer cover extends downwards to form a connecting panel; two sides of the connecting panel protrude to form a rotating shaft portion; the first outer shell is connected to the first inner shell to form a limiting rotating hole; and the rotating shaft is arranged in the limiting rotating hole.

The present disclosure further provides a hand warmer assembly. The hand warmer assembly includes at least one hand warmer unit and the charging case described above.

The hand warmer unit is provided with a second circuit board, a heating element, a second battery, and a second charging unit; the heating element, the second battery, and the second charging unit are all electrically connected to the second circuit board; when the hand warmer unit is placed in the placement chamber, the second charging unit is close to or in contact with the first charging unit; the first charging unit is configured to output the electrical energy, which is output by the first circuit board, to the second charging unit; and the second charging unit charges, via the second circuit board, the second battery with the electrical energy output by the first charging unit.

Further, the first charging unit is a conductive probe; the conductive probe is arranged at the bottom of the placement chamber; the second charging unit is a charging contact; the charging contact is located at a bottom of the hand warmer unit; and the charging contact is in contact with the conductive probe when the hand warmer unit is placed in the placement chamber.

Further, a position, corresponding to the charging contact, on the hand warmer unit is recessed inwards to form a groove; an embedded block is arranged at a position, corresponding to the groove, on the placement chamber; and the embedded block is arranged in the groove when the hand warmer unit is placed in the placement chamber.

Further, there are two hand warmer units, namely a first hand warmer and a second hand warmer; there are two placement chambers; and the first hand warmer and the second hand warmer are detachably connected to each other.

Further, the first hand warmer includes a first outer surface and a first connecting surface opposite to the first outer surface; a first connecting portion is arranged on the first connecting surface; the second hand warmer includes a second outer surface and a second connecting surface opposite to the second outer surface; a second connecting portion is arranged on the second connecting surface; the first connecting portion is connected to the second connecting portion in one of the following manners: a buckle, a hook and loop fastener, and magnetic suction of a plurality of magnetic suction assemblies, so that the first connecting surface is connected to the second connecting surface; and the first hand warmer and the second hand warmer are combined into a whole.

Further, the first connecting portion includes a first clamping slot and a first buckle; the first clamping slot and the first buckle are respectively located at two ends of the hand warmer unit; the second connecting portion includes a second clamping slot and a second buckle; the first buckle is clamped with the second clamping slot when the first hand warmer and second hand warmer are assembled together; and the second buckle is clamped with the first clamping slot when the first hand warmer and second hand warmer are assembled together.

Further, the hand warmer unit is further provided with a second charging interface configured to be externally connected with a power cable.

Further, the capacity of the first battery is at least three times greater than the capacity of the second battery.

Beneficial effects of the present disclosure are as follows: The placement chamber configured to accommodate the hand warmer unit is provided on the charging case, and the first charging unit configured to supply power to the hand warmer unit is configured on the charging case. In this way, when the hand warmer unit is stored and placed in the placement chamber, the first charging unit can be close to or in contact with the hand warmer unit to enable the first charging unit to transmit the electrical energy output by the first circuit board from the first battery to the second charging unit, so as to charge the hand warmer unit. If a user carries the charging case at outdoors, the user can charge the hand warmer unit when the hand warmer unit runs out of power.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

5

6

Figure 22:
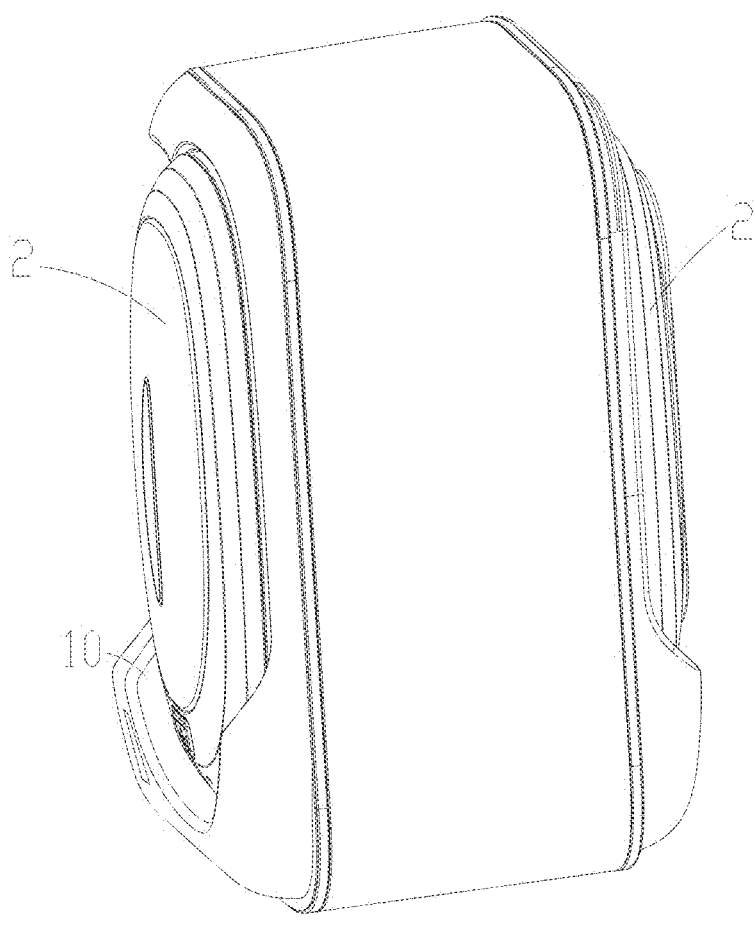
Figure 23:
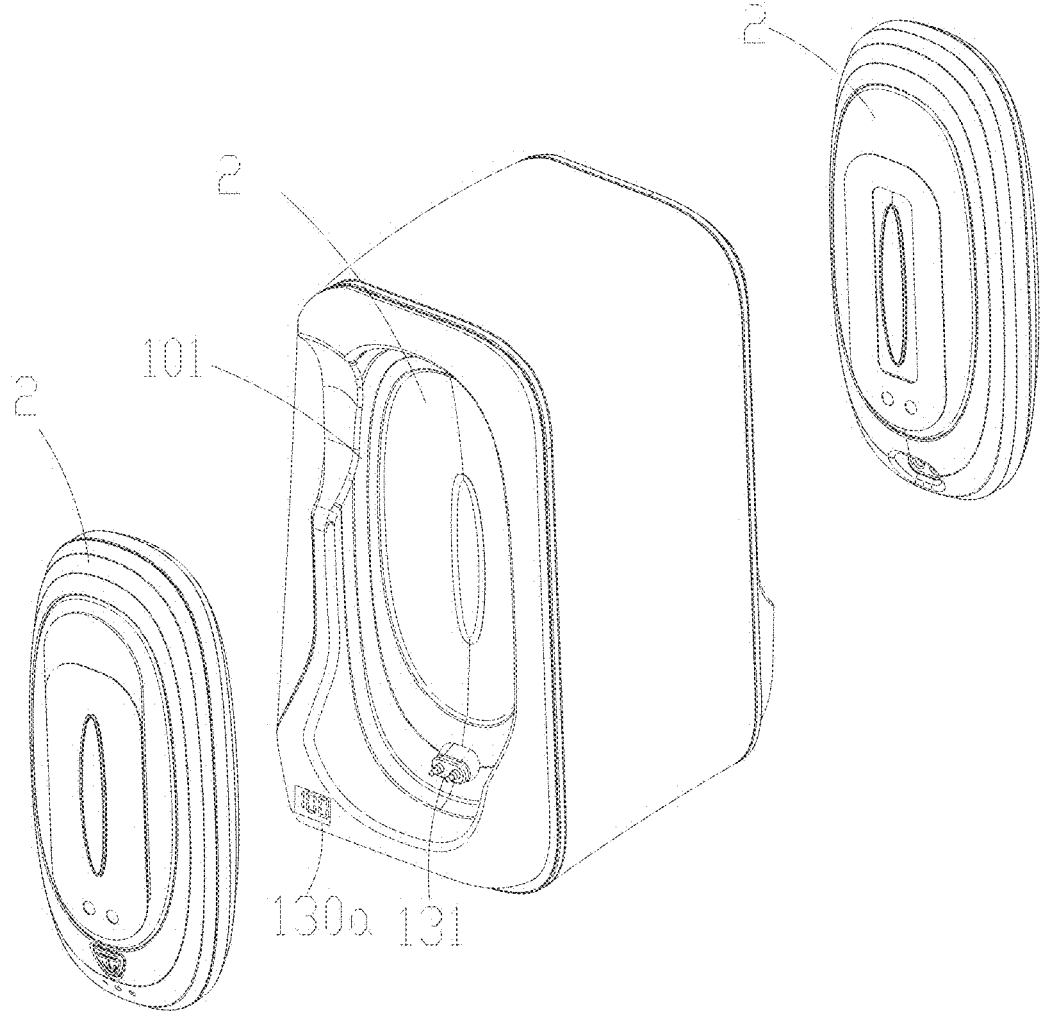
Figure 24:
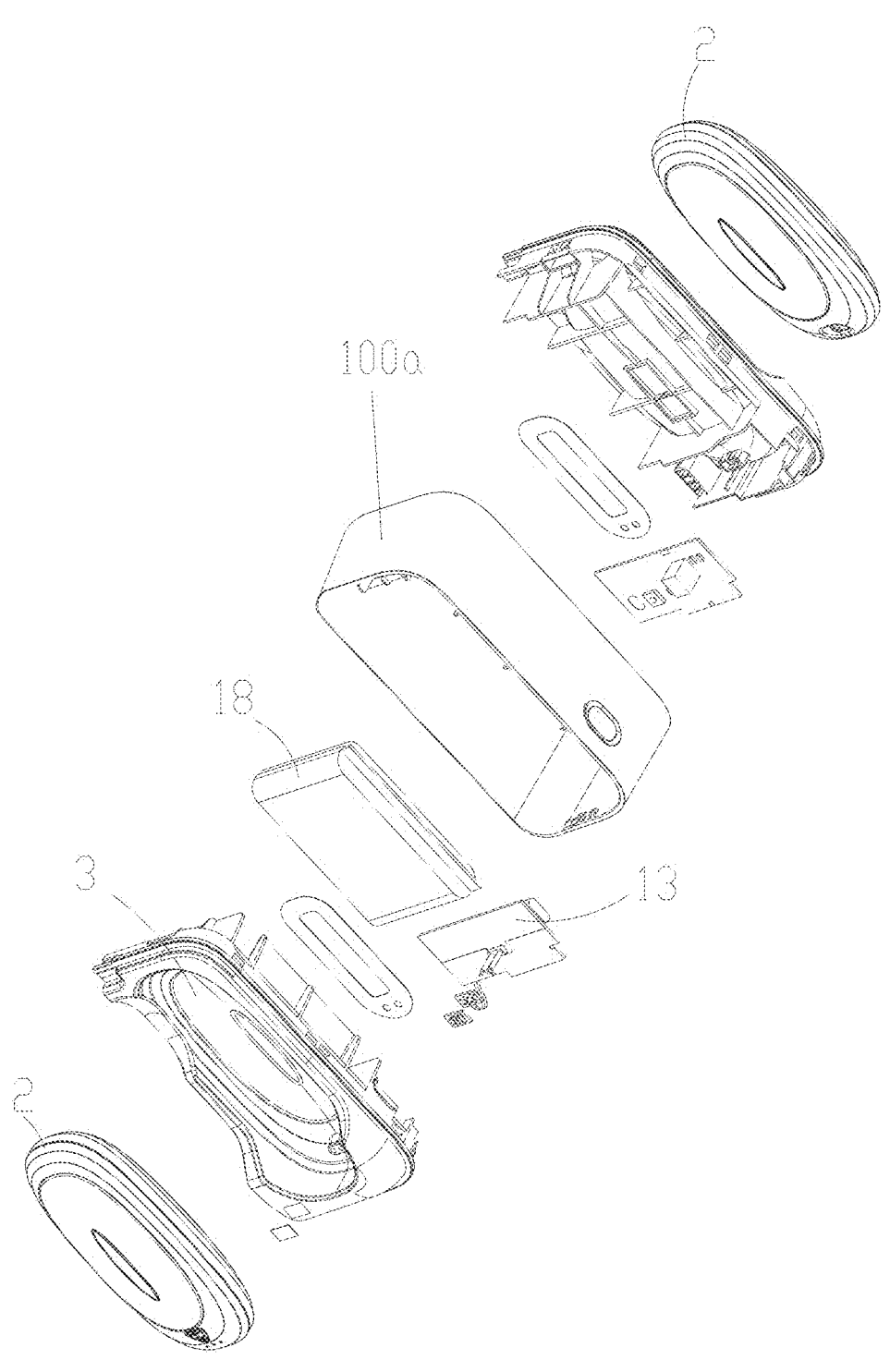
Figure 25:
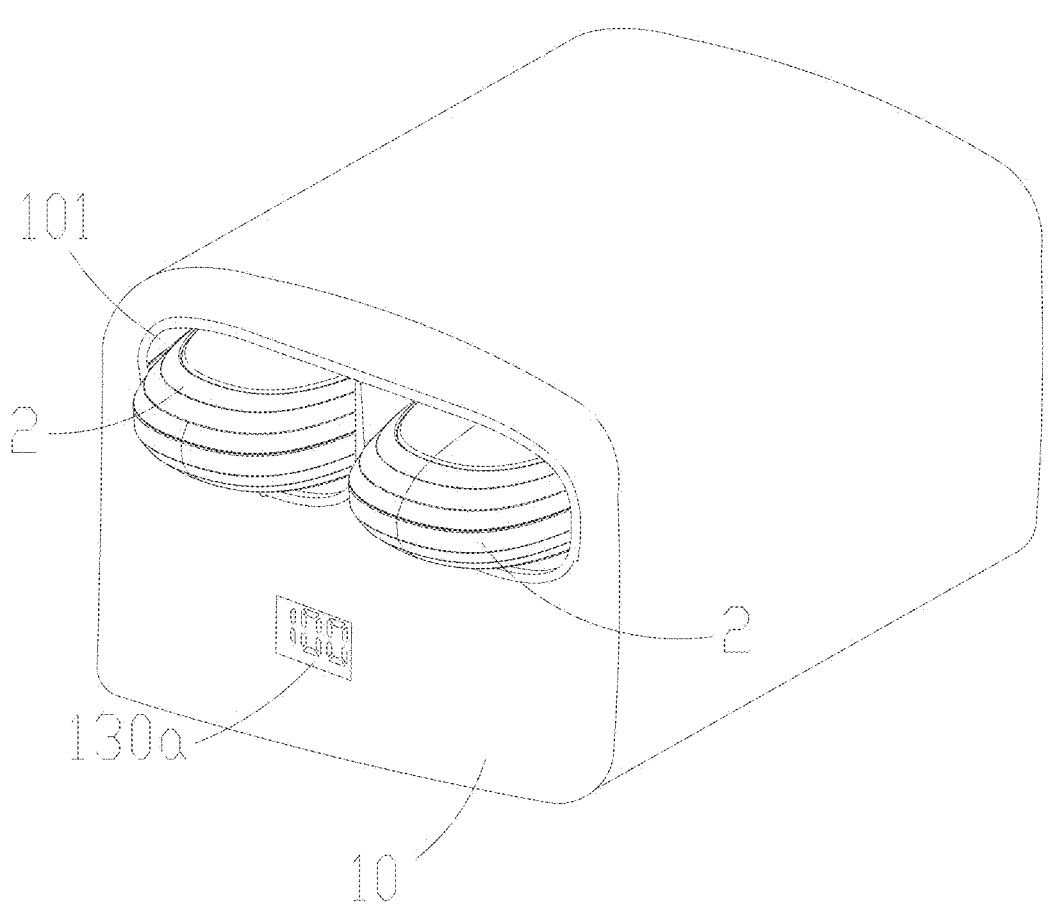
Figure 26:
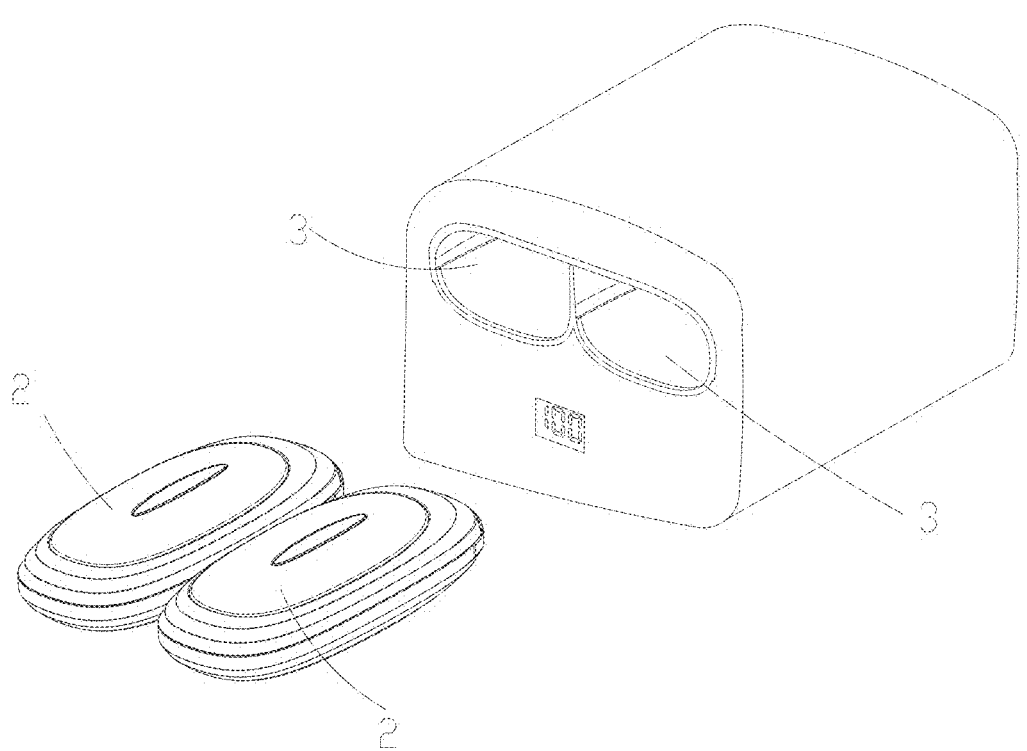
Figure 27:
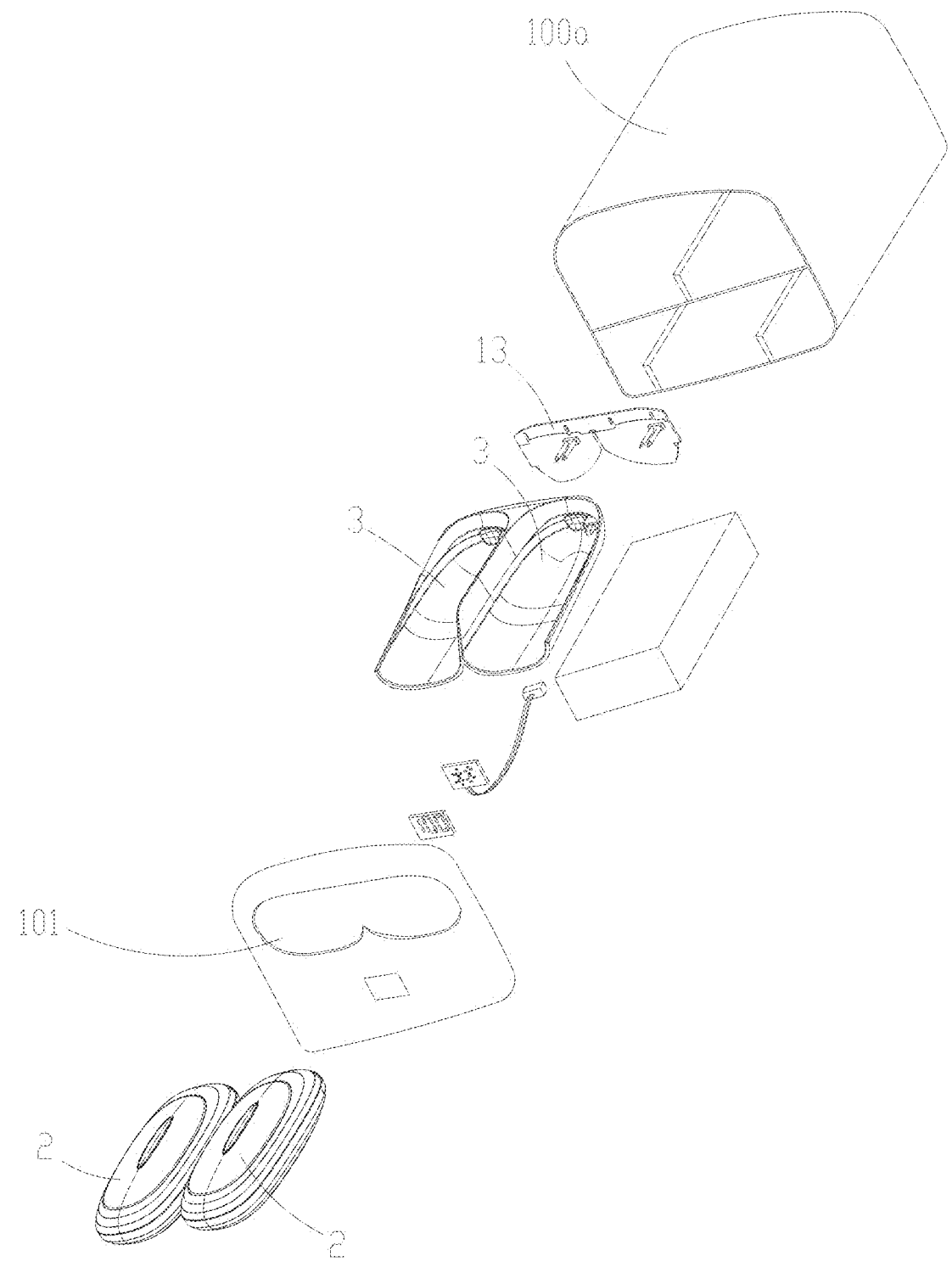
Figure 28:
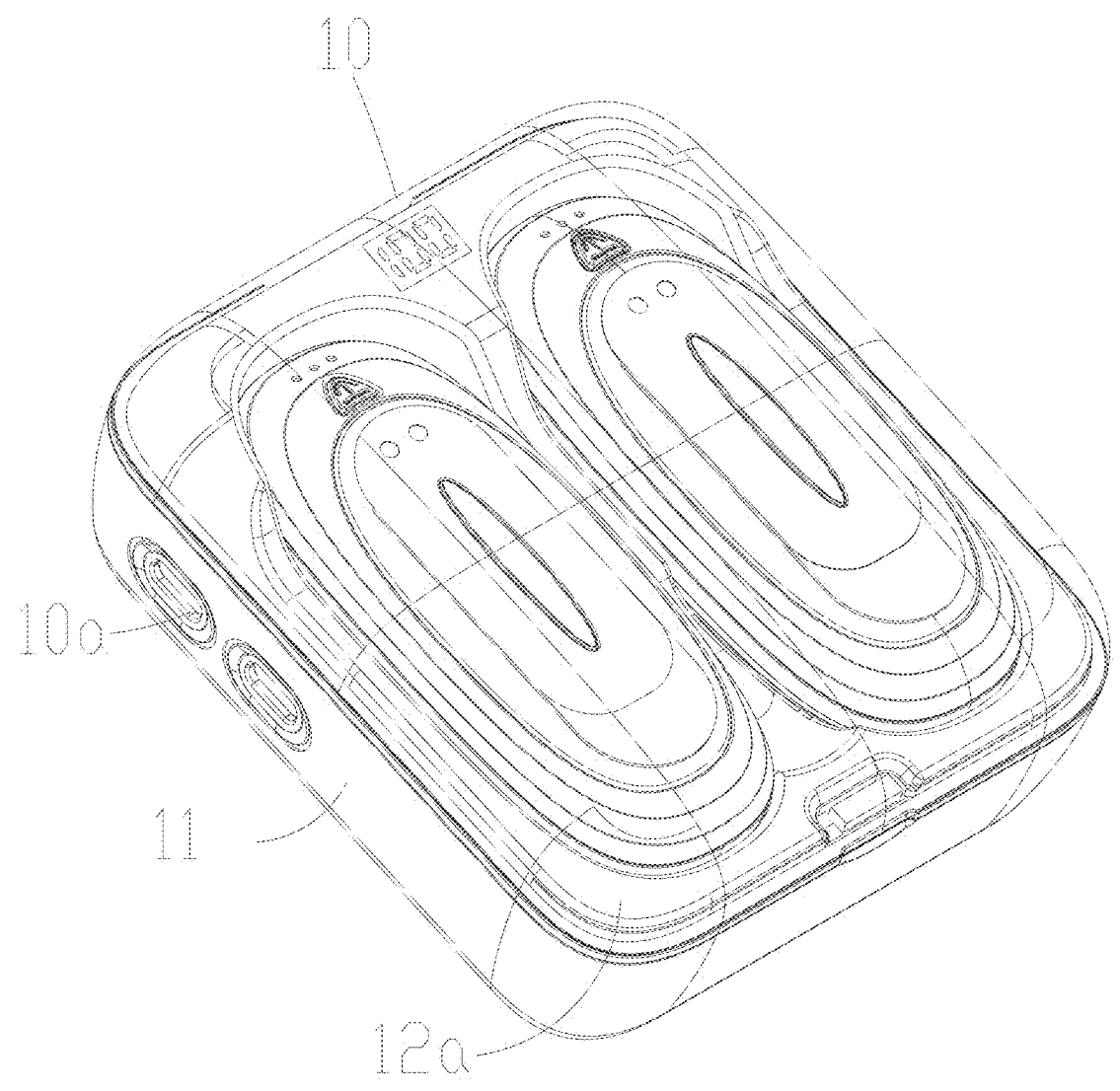
Figure 29:
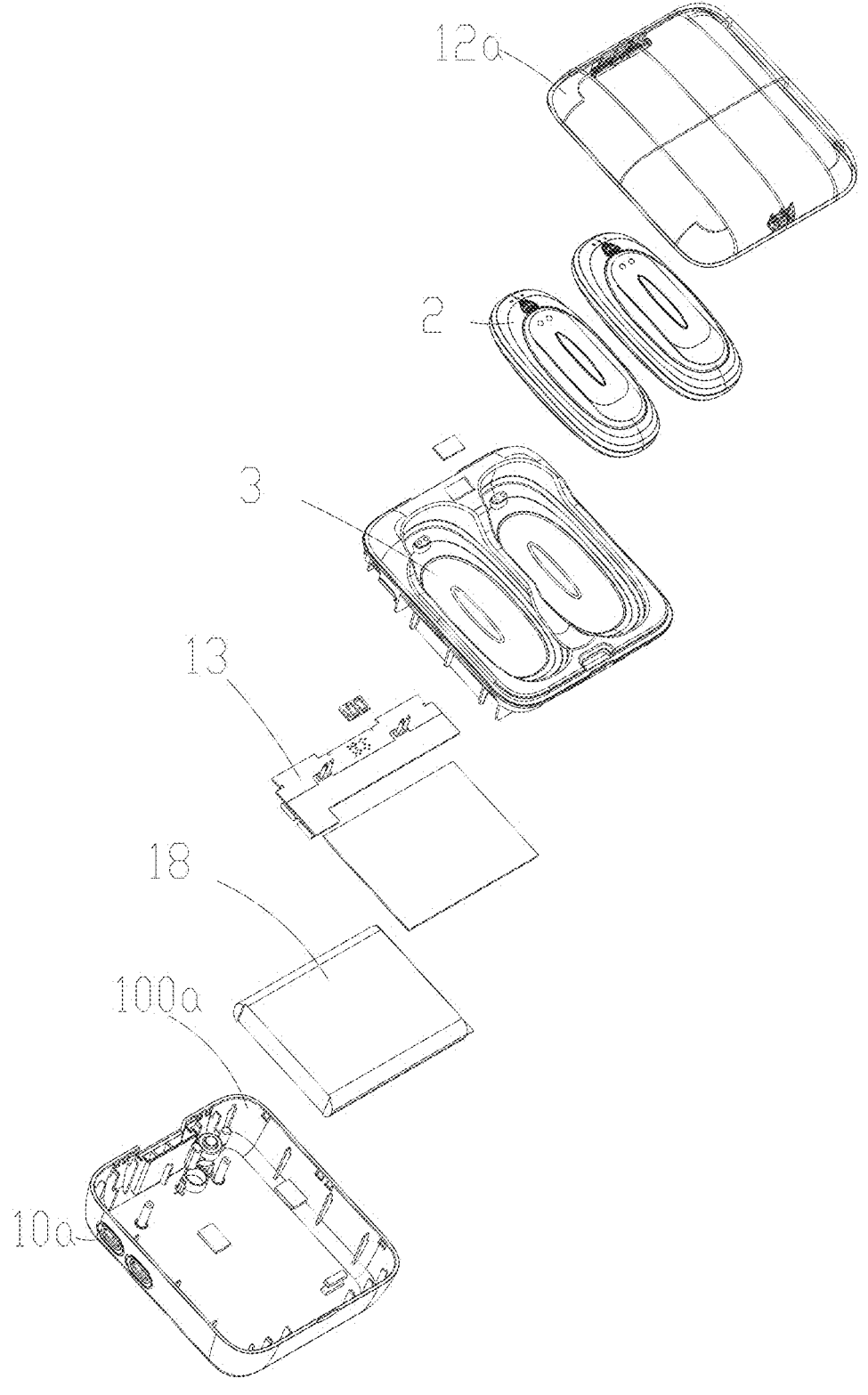
Figure 30:
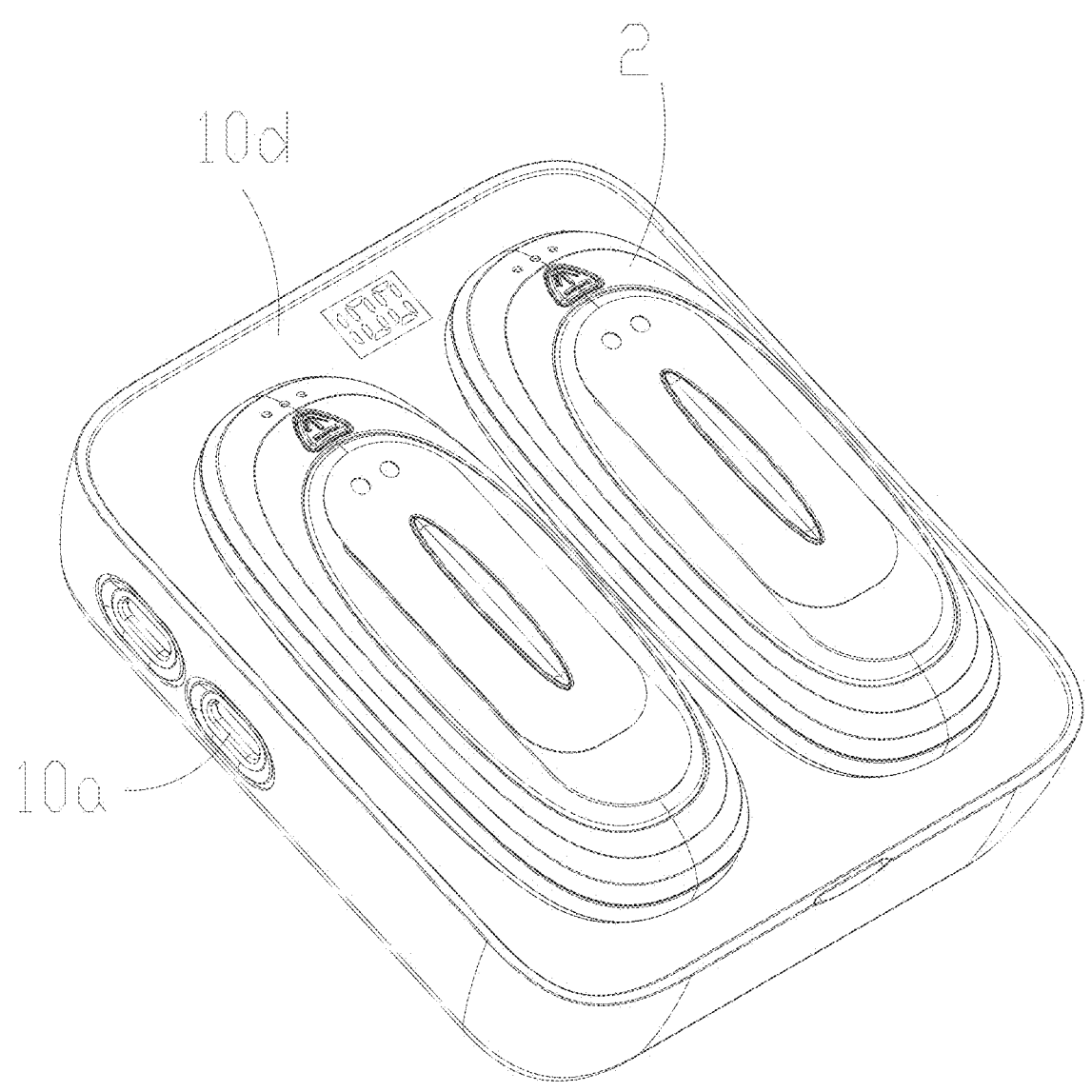
Figure 31:
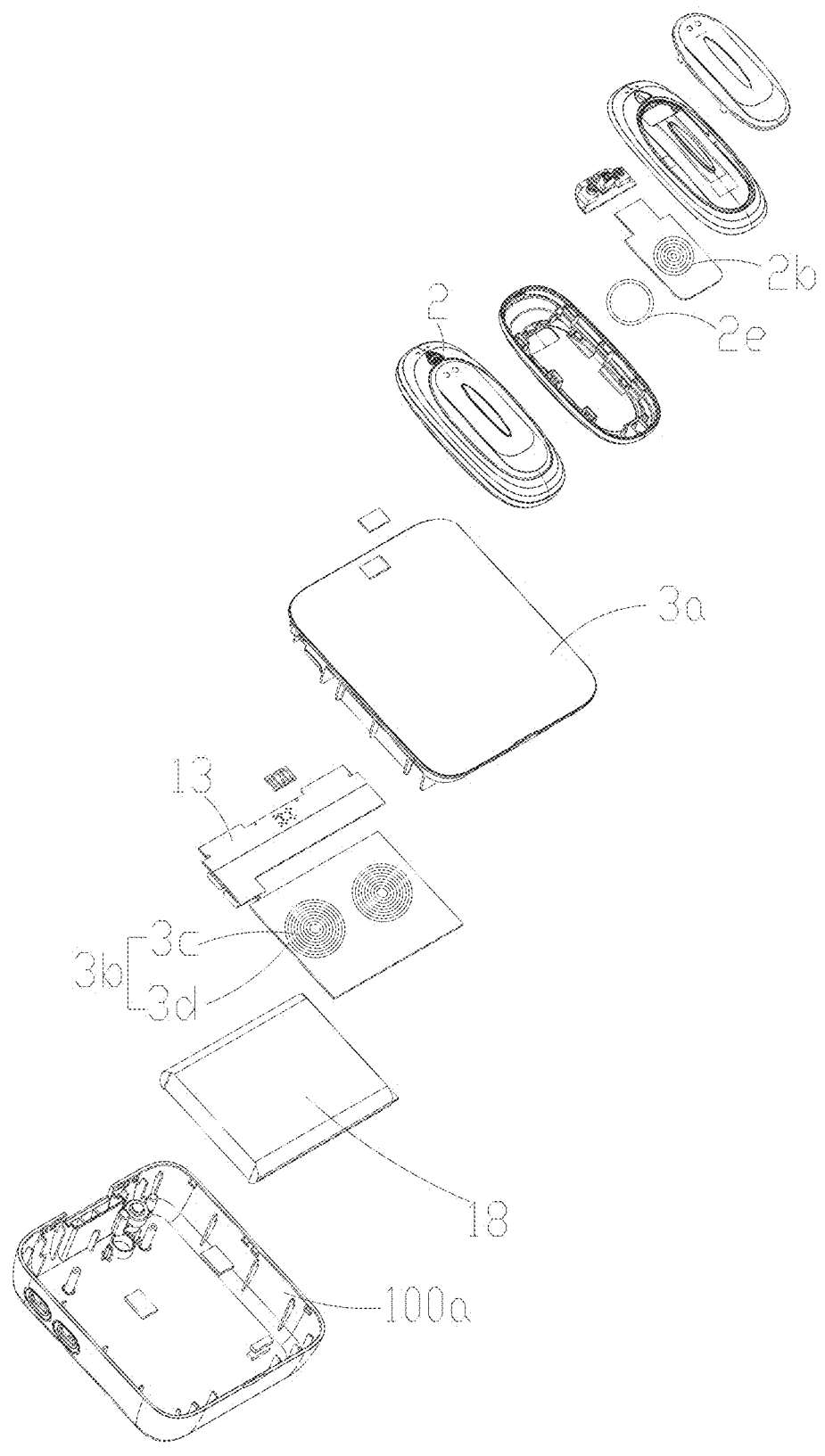

FIG. 22 is a schematic diagram of a portable hand warmer charging case and hand warmer unit in charging state according to further another embodiment of the present disclosure;

FIG. 23 shows the hand warmer unit taken out of the charging case of FIG. 22;

FIG. 24 is an exploded view of FIG. 23;

FIG. 25 is a schematic diagram of a portable hand warmer charging case and hand warmer unit in charging state according to further another embodiment of the present disclosure;

FIG. 26 shows the hand warmer unit taken out of the charging case of FIG. 25;

FIG. 27 is an exploded view of FIG. 26;

FIG. 28 is a schematic diagram of a portable hand warmer charging case and hand warmer unit in charging state according to further another embodiment of the present disclosure;

FIG. 29 is an exploded view of FIG. 28;

FIG. 30 is a schematic diagram of a portable hand warmer charging case and hand warmer unit in charging state according to further another embodiment of the present disclosure;

FIG. 31 is an exploded view of FIG. 30.

Figure 32:
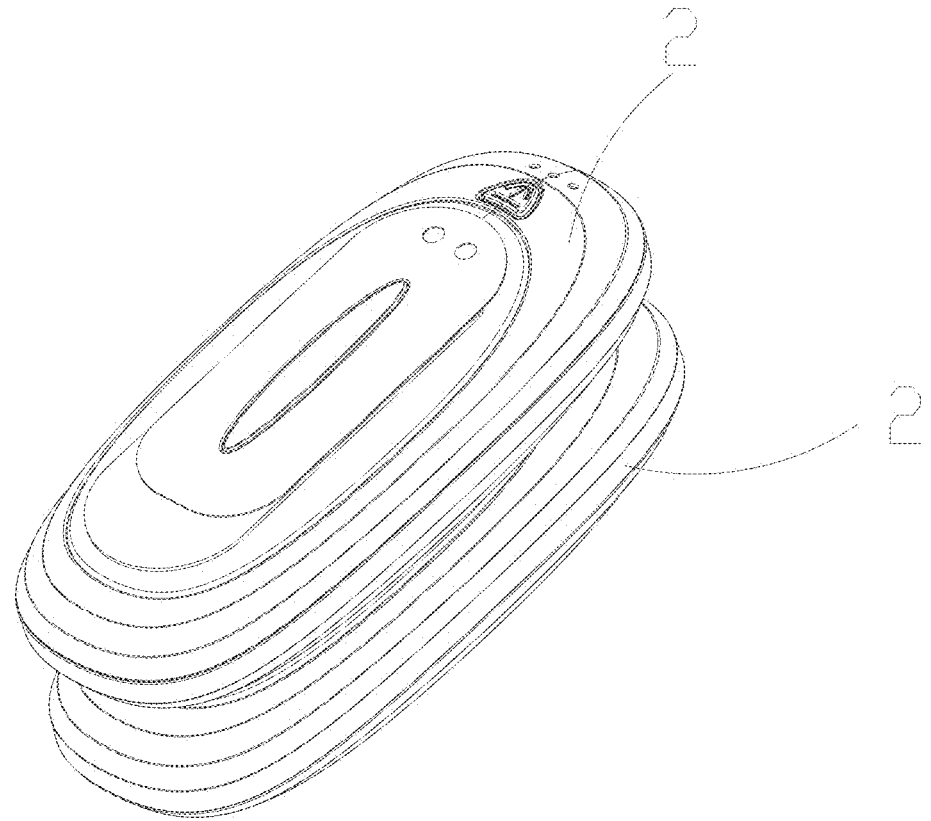

FIG. 32 shows two hand warmer units are combined together by magnetic attraction manner.

DETAILED DESCRIPTION OF THE EMBODIMENTS

The accompanying drawings in the embodiment of the present disclosure are combined. The technical scheme in the embodiment of the present disclosure is clearly and completely described, Obviously, the described embodiment is only a part of the embodiment of the present disclosure, but not all embodiments are based on the embodiment of the present disclosure, and all other embodiments obtained by ordinary technicians in the field on the premise of not doing creative work belong to the protection range of the present disclosure.

Referring to FIG. 1 to FIG. 8, a portable hand warmer charging case 1 in the embodiments of the present disclosure is provided.

The portable hand warmer charging case 1 includes a case body 10. A placement chamber 3 configured to place a hand warmer unit 2 for charging is provided on the case body 10. The case body 10 is provided with a first circuit board 13, a first charging unit 131, and a first battery 18; the first battery 18 and the first charging unit 131 are electrically connected to the first circuit board 13; when the hand warmer unit 2 is placed in the placement chamber 3, the first circuit board 13 is configured to output electrical energy, which is output by the first battery 18, from the first charging unit 131; and the first charging unit 131 is configured to be adapted to a second charging unit 24 on the hand warmer unit 2 for use and transmit the electrical energy output by the first circuit board 13 to the second charging unit 24 on the hand warmer unit 2.

In this embodiment, the placement chamber 3 configured to accommodate the hand warmer unit 2 is provided on the charging case 1, and the first charging unit 131 configured to supply power to the hand warmer unit 2 is configured on the charging case 1. In this way, when the hand warmer unit 2 is stored and placed in the placement chamber 3, the first charging unit 131 can be close to or in contact with the hand warmer unit 2 to enable the first charging unit 131 to transmit the electrical energy output by the first circuit board 13 from the first battery 18 to the second charging unit 24, so as to charge the hand warmer unit 2. If a user carries the charging case 1 at outdoors, the user can charge the hand warmer unit 2 when the hand warmer unit 2 runs out of power. The problem of inconvenience of charging of the existing hand warmer unit 2 at outdoors is solved.

In an embodiment, since the hand warmer unit 2 is designed to be used for the hands of a user, most hand warmer units 2 are generally flat. The thickness of the placement chamber 3 is adapted to the thickness of the hand warmer unit 2 to make the overall appearance of the charging case 1 harmonious. The first circuit board 13 is located at the bottom of the placement chamber 3, and the first battery 18 is located behind the case body 10. Of course, in other embodiments, the first circuit board 13 and the first battery 18 may be both located at the bottom, back, or front side of the placement chamber 3. Or, the first circuit board 13 may be located in front of the placement chamber 3, and the first battery 18 may be located at the back of the placement chamber 3.

In an embodiment, the first circuit board 13 is provided with a battery level indicator lamp 133 configured to indicate a battery level state of the first battery 18 and/or a charging state of the hand warmer unit 2, so that a user can learn the battery level of the first battery 18 and whether the hand warmer unit 2 is fully charged.

In an embodiment, the indicator lamp unit 130 includes a plurality of light-emitting bodies 135 arranged on the first circuit board 13, and the plurality of light-emitting bodies 135 are arranged side by side. Of course, in other embodiments, the plurality of light-emitting bodies 135 can alternatively be arranged in a surrounding manner, irregularly arranged, distributed in an arc shape, or the like. Therefore, if the first battery 18 only has a half battery level, the first circuit board 13 can control half of the light-emitting bodies 135 to emit light. If the first battery 18 has full battery level, the first circuit board 13 can control all the light-emitting bodies 135 to emit light, so that a user can learn the battery level of the first battery 18. Of course, the color of light emitted by the light-emitting bodies 135 can alternatively be used to indicate the battery level of the first battery 18. For example, if the first battery 18 has full battery level, the light-emitting bodies 135 emit green light; and if the first battery 18 has low battery, the light-emitting bodies 135 emit red light. The light-emitting bodies 135 can be light-emitting diode (LED) lamps, LEDs, or the like.

In an embodiment, the case body 10 is further provided with a light guide hood 14; the light guide hood 14 is provided with an accommodating slot 141 at a position corresponding to each light-emitting body 135; the light-emitting body 135 is located in the accommodating slot 141; a first light guide hole 142 that is communicated with the accommodating slots 141 is provided on the light guide hood 14; and a second light guide hole 1112 is provided at a position, corresponding to the first light guide hole 142, on the case body 10. Specifically, the light guide hood 14 is made of an opaque material, which means that the light from the light-emitting bodies 135 can only pass through the first light guide hole 142 and then exit from the second light guide hole 1112, which prevents the problem of poor indication effect caused by the mutual impact of the light between the plurality of light-emitting bodies 135.

In an embodiment, the indicator lamp unit 130 includes a battery level indicator lamp 133 and a charging state indicator lamp 132, and the charging state indicator lamp 132 is located next to the battery level indicator lamp 133. The battery level indicator lamp 133 can indicate a battery level of the first battery 18 according to the number of the light-emitting bodies that are lit up, and the charging state indicator lamp 132 indicates a charging state of the hand warmer unit 2 according to the color of the emitted light, to facilitate use.

In an embodiment, the first circuit board 13 is provided with a function button 134; and the case body 10 is provided with a pressing member 15 connected to the function button 134. When the hand warmer unit 2 is placed in the placement chamber 3, a user can press the function button 134 by pressing the pressing member 15. The first circuit board 13 detects an electrical signal of the function button 134 and outputs the electrical energy of the first battery 18 from the first charging unit 131 to control the charging of the hand warmer unit 2. Of course, by pressing the function button 134, the first circuit board 13 can further drive the indicator lamp to be turned on, so that a user can learn the remaining power of the first battery 18.

In the above embodiments, a first charging interface 136 is provided on the first circuit board 13; and a first avoidance hole 1111 configured to avoid the first charging interface 136 is provided on the case body 10. The first charging interface 136 is configured to be externally connected to a power supply. After the power supply is connected, the first battery 18 can be charged via the first circuit board 13, so that a user can charge the first battery 18 if the charging case 1 has low battery. Of course, in other embodiments, the charging case 1 can further use wireless charging to charge the first battery 18.

In an embodiment, for the structural compactness and beauty, the indicator lamp unit 130, the function button 134, and first charging interface 136 are arranged side by side in a thickness direction of the charging case 1; and the function button 134 is located between the indicator lamp unit 130 and the first charging interface 136.

In the above embodiment, the case body 10 includes a main body 11 and a cover body 12 connected to the main body 11 to form the placement chamber 3; and the first circuit board 13, the first battery 18, the pressing member 15, the first avoidance hole 1111, and the second light guide hole 1112 are all located on the main body 11. The cover body 12 is used to cooperate with the main body 11 to form the closed placement chamber 3. When the hand warmer unit 2 is placed on the placement slot, the hand warmer unit 2 can be completely wrapped to achieve an effect of protecting the hand warmer unit 2, so that the hand warmer unit is convenient to carry when people go out. Of course, in other embodiments, the cover body 12 may not be needed, and the structure of the case body 10 is not limited here.

For the structural compactness and case of production and manufacturing of the product, the placement chamber 3 includes a first placement slot 31; the first charging unit 131 is a conductive probe; the conductive probe is arranged at a bottom of the first placement slot 31; the main body 11 includes a first outer cover 111 and a first inner shell 112 connected to the first outer cover 111 to form the first placement slot 31, a first mounting chamber 17, and a second mounting chamber 16; the first inner shell 112 is located on an inner side of the first outer cover 111; the first mounting chamber 17 is located below the first placement slot 31; and the first circuit board 13 and the light guide hood 14 are arranged in the first mounting chamber 17. The first battery 18 is arranged in the second mounting chamber 16, and the second mounting chamber 16 is located behind the first placement slot 31. The pressing member 15, the first avoidance hole 1111, and the second light guide hole 1112 are all located on the first outer cover 111.

In an embodiment, the cover body 12 is rotatably connected to the main body 11. Of course, in other embodiments, the cover body 12 and the main body 11 may be further connected to each other through magnetic suction, a buckle, or the like.

In an embodiment, the placement chamber 3 includes a second placement slot 32; the cover body 12 includes a second outer cover 121 and a second inner shell 122 connected to the second outer cover 121 to form the second placement slot 32; the second inner shell 122 is at least partially located on an inner side of the second outer cover 121; a bottom of the second outer cover 121 extends downwards to form a connecting panel 1211; two sides of the connecting panel 1211 protrude to form a rotating shaft portion 1212; The first outer shell 111 is connected to the first inner shell 112 to form a limiting rotating hole 1122. The rotating shaft portion 1212 is arranged in the limiting rotating hole 1122 to achieve rotatable connection between the cover body 12 and the main body 11. Furthermore, one side of the cover body 12 away from the rotating shaft portion 1212 can be stably connected to the main body 11 through magnetic suction, a buckle, or the like, so as to prevent the cover body 12 from being automatically opened.

Based on the above charging case 1, this embodiment further provides a hand warmer assembly.

Referring to FIG. 1 to FIG. 10, the hand warmer assembly includes at least one hand warmer unit 2 and the charging case 1 as described above. The hand warmer unit 2 is provided with a second circuit board 23, a heating element 22, a second battery 21, and a second charging unit 24; and the heating element 22, the second battery 21, and the second charging unit 24 are all electrically connected to the second circuit board 23. When the hand warmer unit 2 is placed in the placement chamber 3, the second charging unit 24 is close to or in contact with the first charging unit 131; the first charging unit 131 is configured to output the electrical energy, which is output by the first circuit board 13, to the second charging unit 24; and the second charging unit 24 charges, via the second circuit board 23, the second battery 21 with the electrical energy output by the first charging unit 131. By the use of the charging case 1, it is convenient for a user to charge the hand warmer unit 2 when the user goes out.

In an embodiment, the first charging unit 131 is a conductive probe, and the conductive probe is arranged at a bottom of the placement chamber 3. The second charging unit 24 is a charging contact. The charging contact is located at a bottom of the hand warmer unit 2. When the hand warmer unit 2 is placed in the placement chamber 3, the charging contact is in contact with the conductive probe to allow the electrical energy output by the first battery 18 to charge the second battery 21 through the first circuit board 13, the conductive probe, the charging contact, and second circuit board 23.

In an embodiment, a position, corresponding to the charging contact, on the hand warmer unit 2 is recessed inwards to form a groove 25; an embedded block 1121 is arranged at a position, corresponding to the groove 25, on the placement chamber 3; and the embedded block 1121 is arranged in the groove 25 when the hand warmer unit 2 is placed in the placement chamber 3.

In an embodiment, the case body 10 and the hand warmer unit 2 can be further fixed through interference fit, magnetic suction, and buckle connection, which can improve the stability of contact between the conductive probe and the charging contact too.

In other embodiments, both the first charging unit 131 and the second charging unit 24 can be coils. Namely, when the hand warmer unit 2 is placed in the placement chamber 3, the first charging unit 131 and the second charging unit 24 are close to and interact with each other, so that the electrical energy output by the first battery 18 charges the second battery 21 through the first circuit board 13, the conductive probe, the charging contact, and the second circuit board 23, achieving wireless charging of the hand warmer unit 2. Or, the first charging unit 131 and the second charging unit 24 can be a male interface and a female interface adapted for use, and can charge the hand warmer unit 2 when the hand warmer unit 2 is placed in the placement chamber 3.

Figure 13:
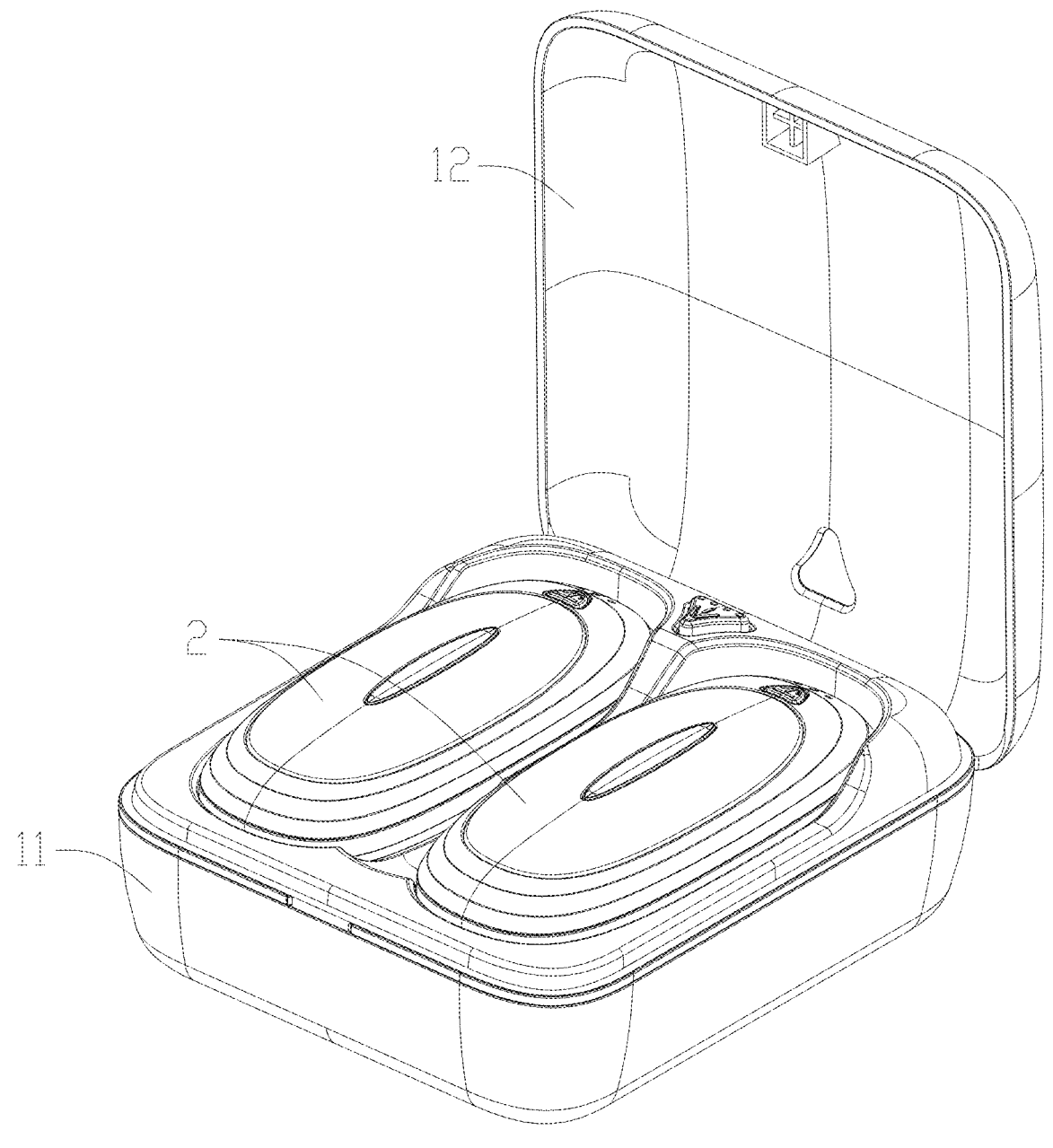
FIG. 13 is a schematic diagram of a hand warmer module of another embodiment of the present disclosure according to another embodiment.
Figure 14:
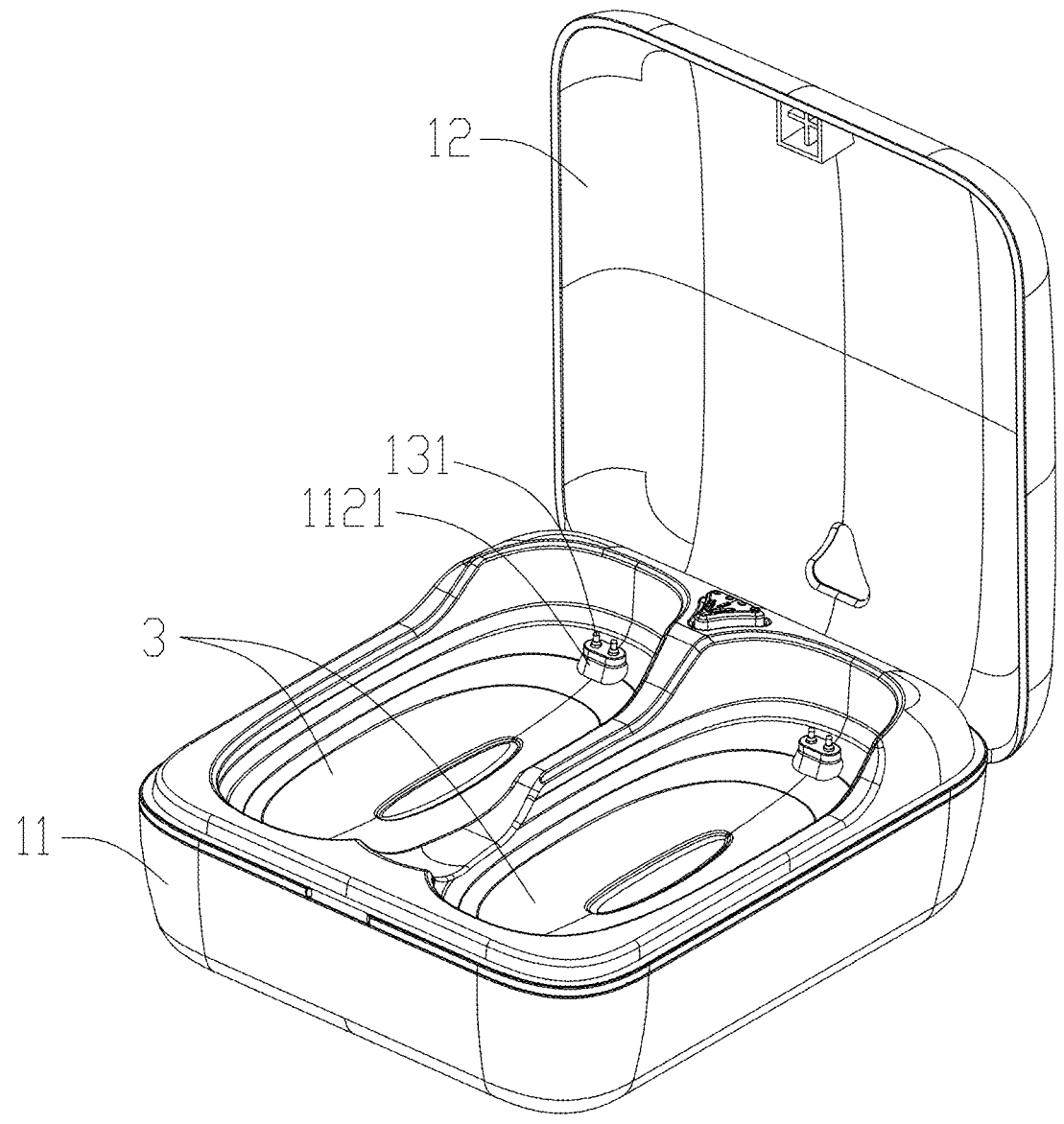
FIG. 14 is a schematic diagram of a charging case of another embodiment of the present disclosure.
Figure 15:
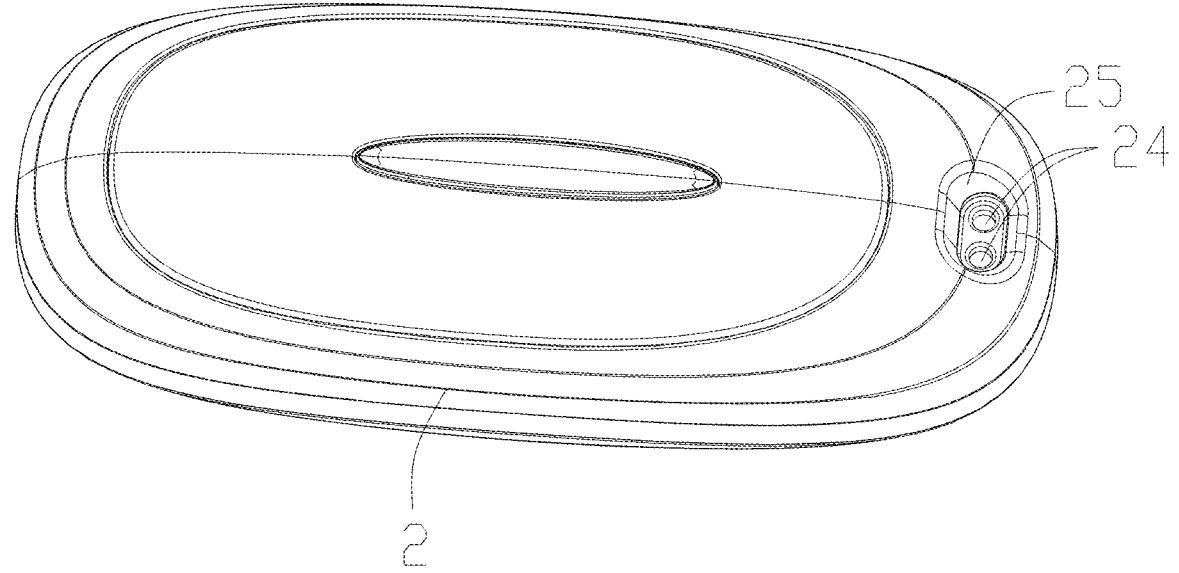
FIG. 15 is a schematic diagram of a hand warmer unit of another embodiment of the present disclosure.

In an embodiment, the charging contact can be arranged at the bottom of the hand warmer unit. Namely, the hand warmer unit 2 is inserted vertically into the placement chamber 3, namely, into the placement chamber 3 in a height direction of the hand warmer unit 2. In other embodiments, the charging contact can be arranged on a side wall of the hand warmer unit 2. Namely, the hand warmer unit 2 can be inserted into the placement chamber 3 in a width direction of the hand warmer unit 2. In other embodiments, the charging contact can alternatively be arranged on an upper or lower surface of the hand warmer unit, so that the hand warmer unit 2 can be placed in the placement chamber 3 in a flat state. Referring to FIG. 13 to FIG. 15, that is, the hand warmer unit 2 can be placed in the placement chamber 3 in a thickness direction of the hand warmer unit 2. The manufacturers can customize the configuration according to their needs.

In an embodiment, there is one placement chamber 3, which means that the charging case 1 is only suitable for charging one hand warmer unit 2.

In an embodiment, there are a plurality of placement chambers 3. Each placement chamber 3 is provided with one first charging unit 131, which means that the charging case 1 can simultaneously charge a plurality of hand warmer unit 2.

Figure 1:
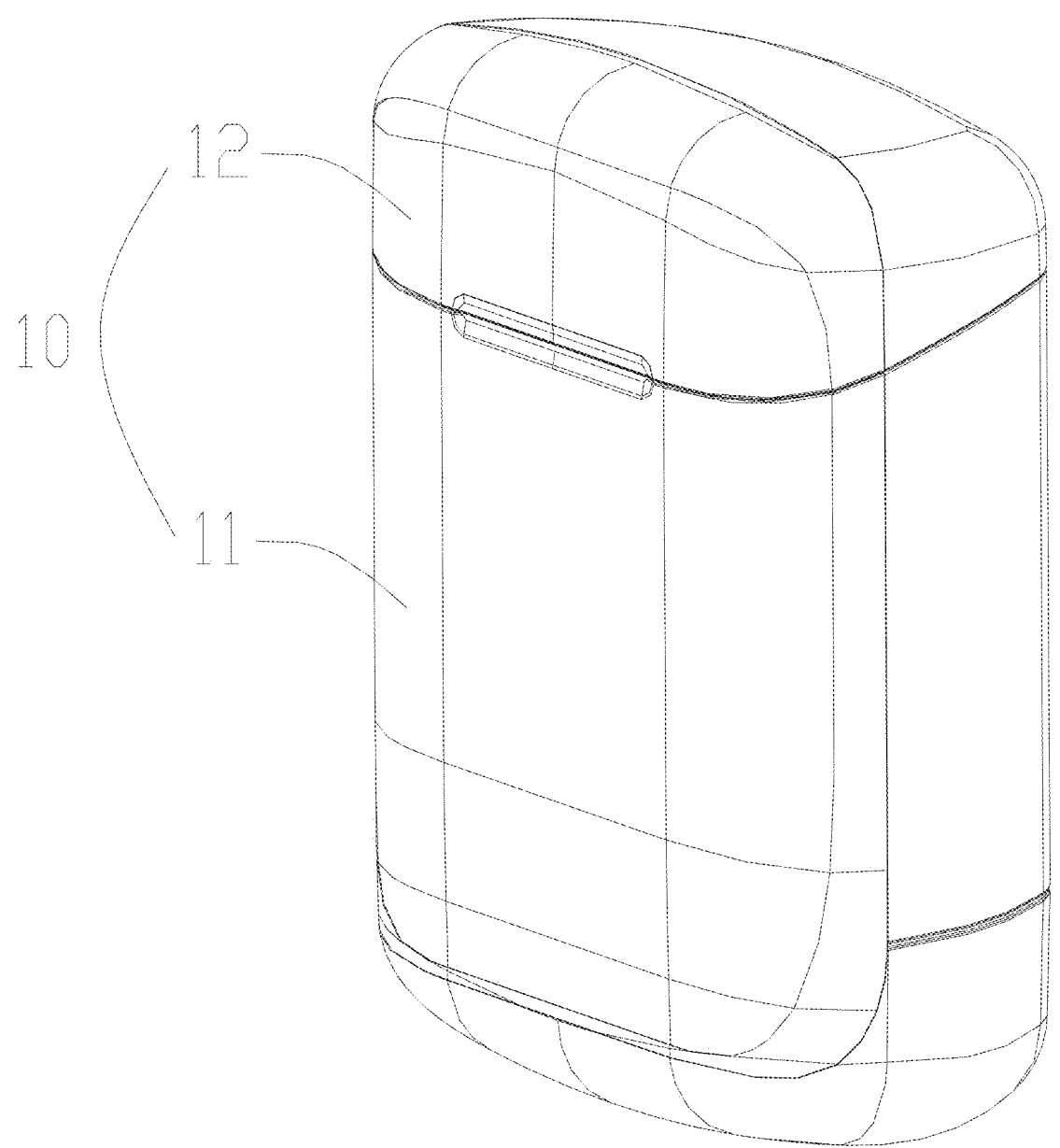
FIG. 1 is a schematic diagram of a charging case of the present disclosure.
Figure 2:
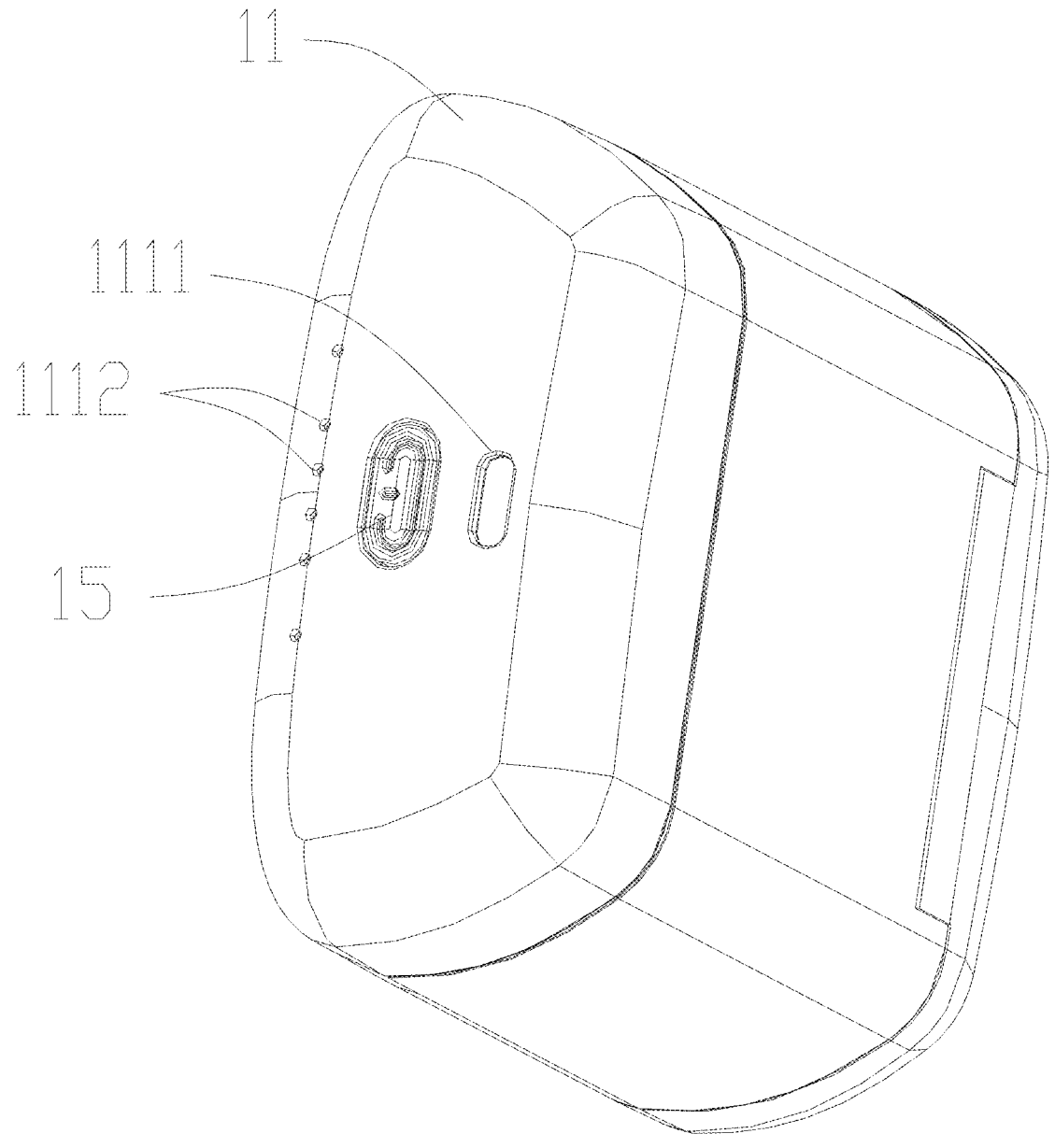
FIG. 2 is a schematic diagram of a charging case in another viewing angle according to the present disclosure.
Figure 3:
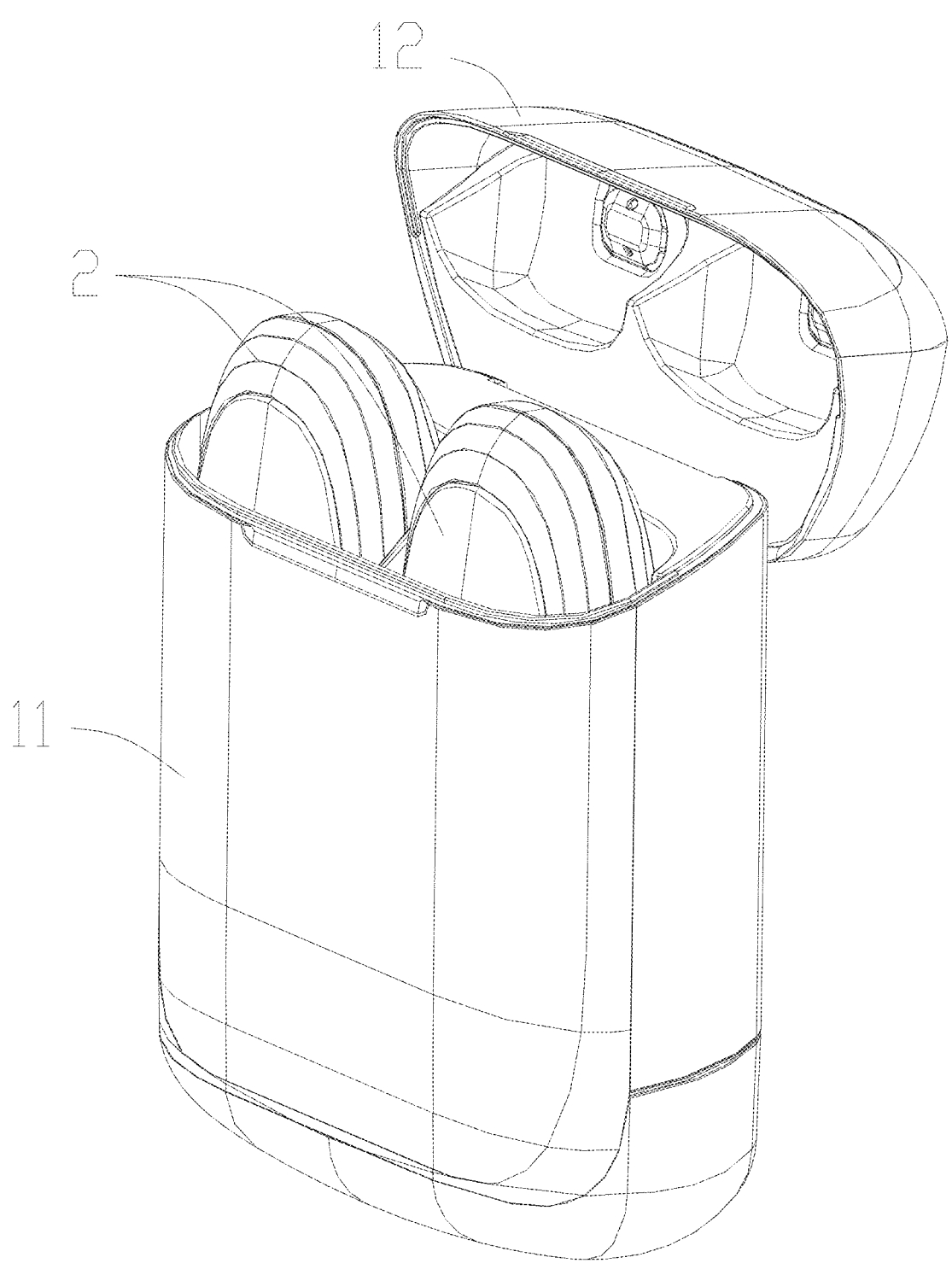
FIG. 3 is a schematic state diagram of a hand warmer assembly according to the present disclosure.
Figure 4:
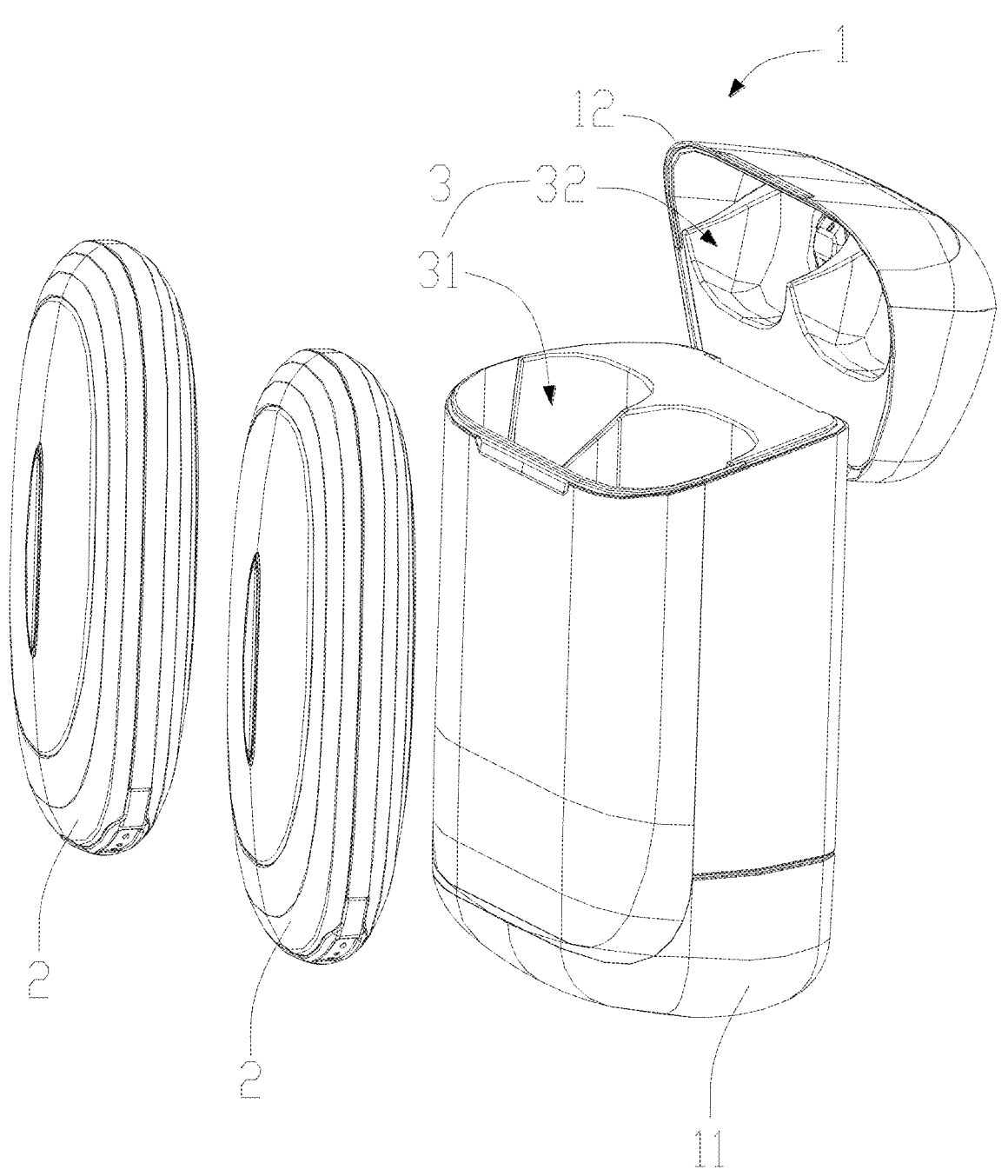
FIG. 4 is a partially exploded diagram of a hand warmer assembly according to the present disclosure.
Figure 5:
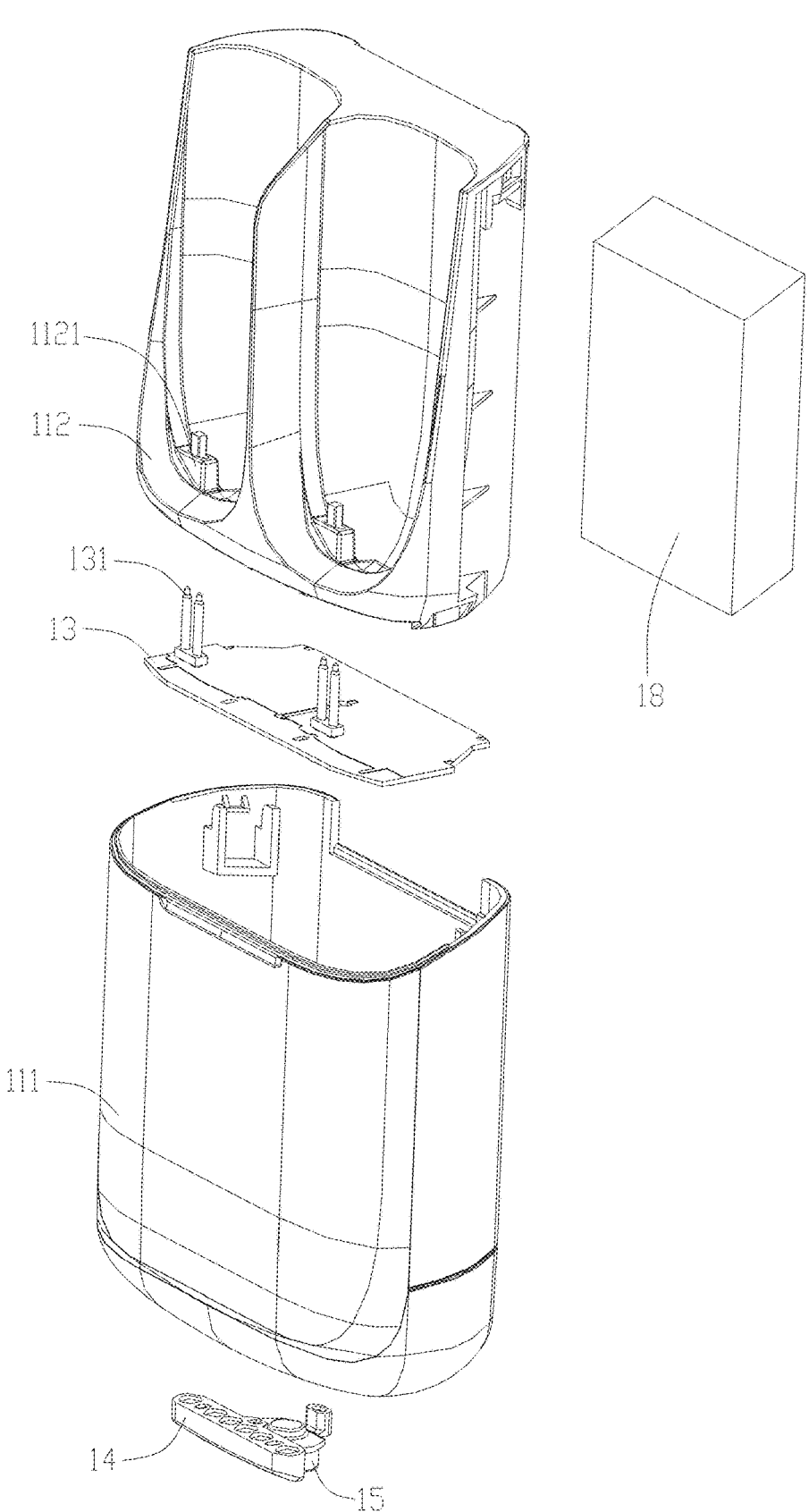
FIG. 5 is an exploded diagram of a main body according to the present disclosure.
Figure 6:
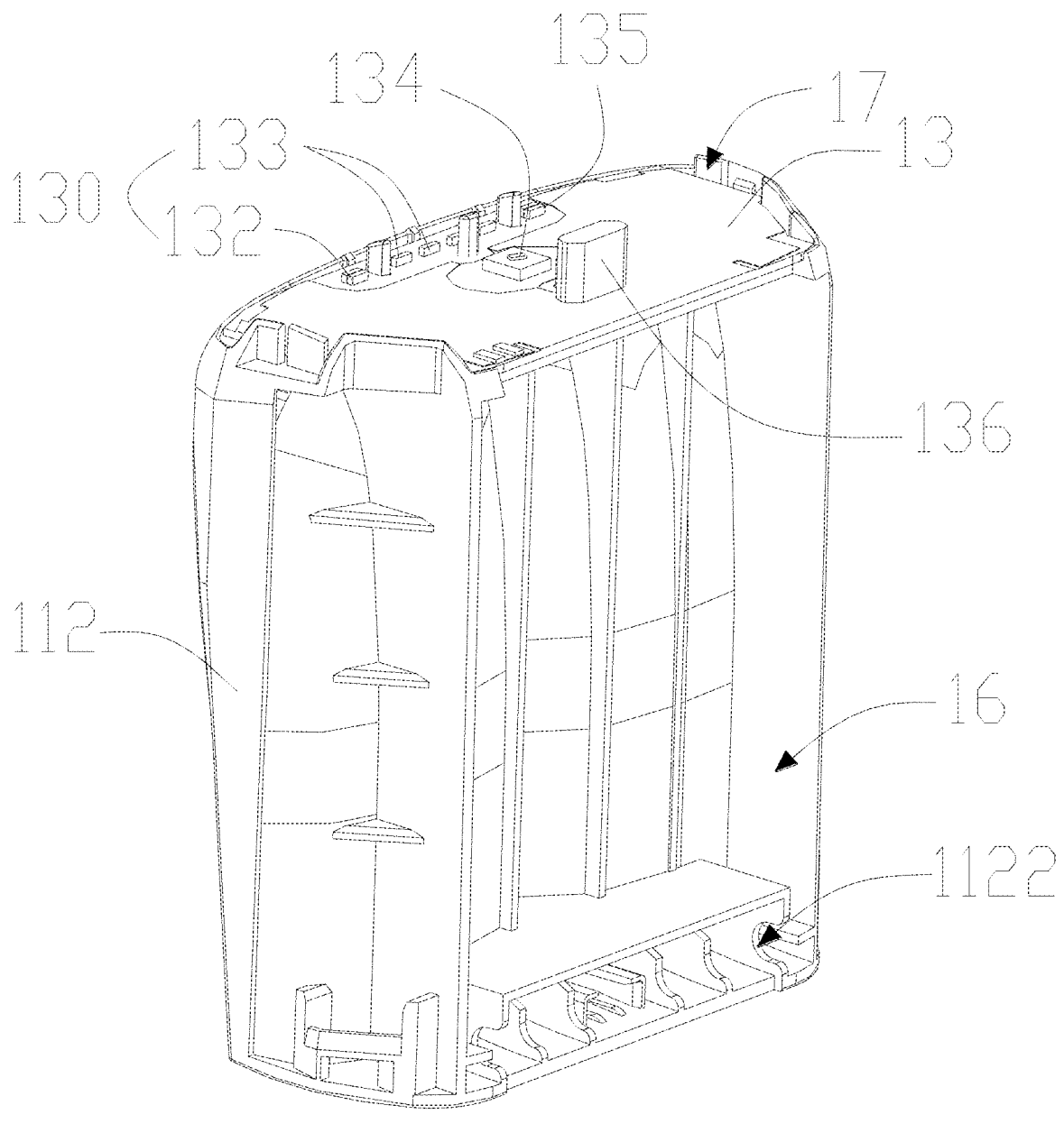
FIG. 6 is a schematic diagram of assembling a first inner shell and a first circuit board according to the present disclosure.
Figure 7:
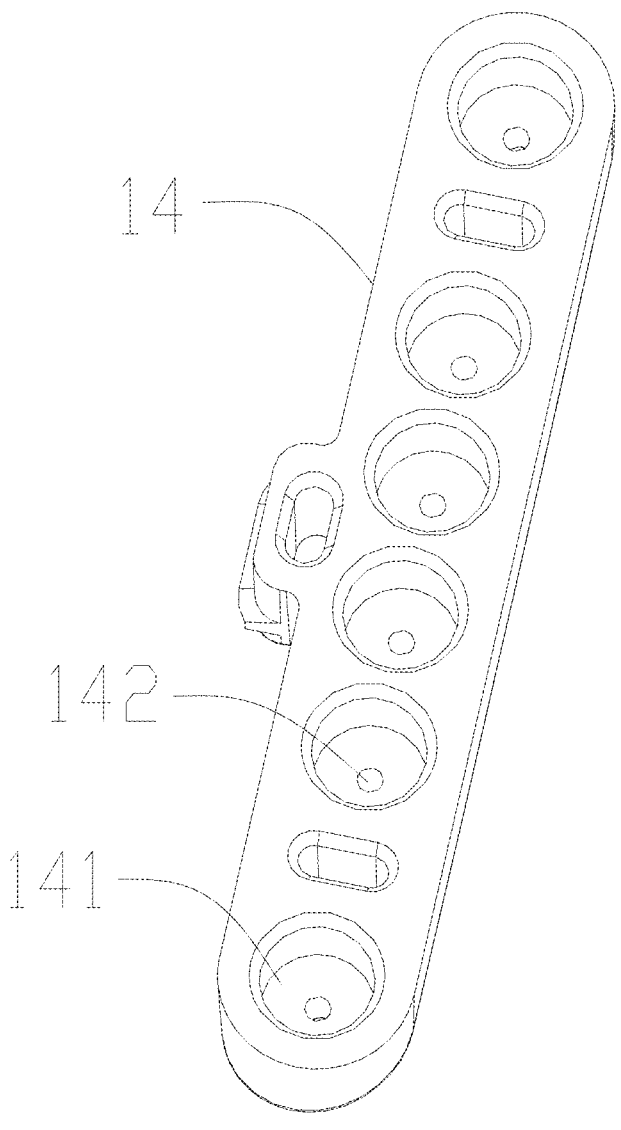
FIG. 7 is a structural diagram of a light guide hood according to the present disclosure.
Figure 8:
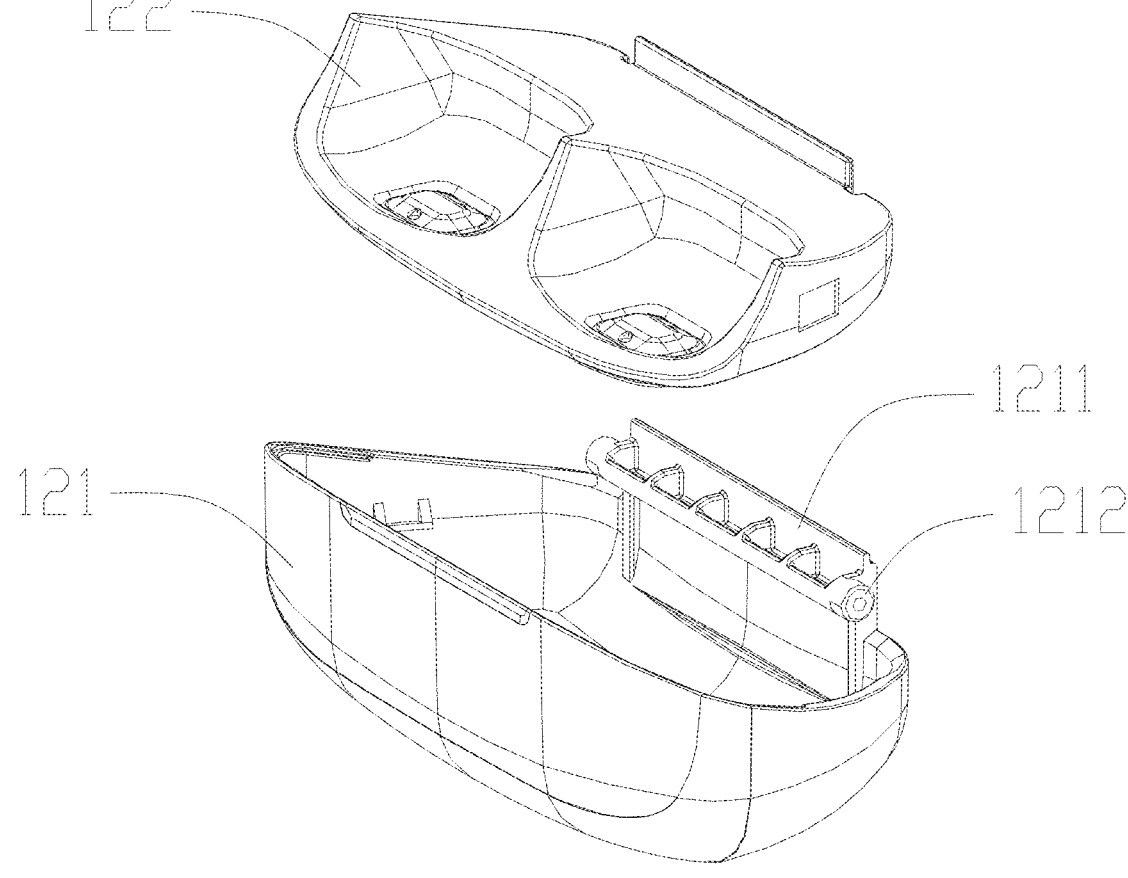
FIG. 8 is an exploded diagram of a cover body according to the present disclosure.
Figure 9:
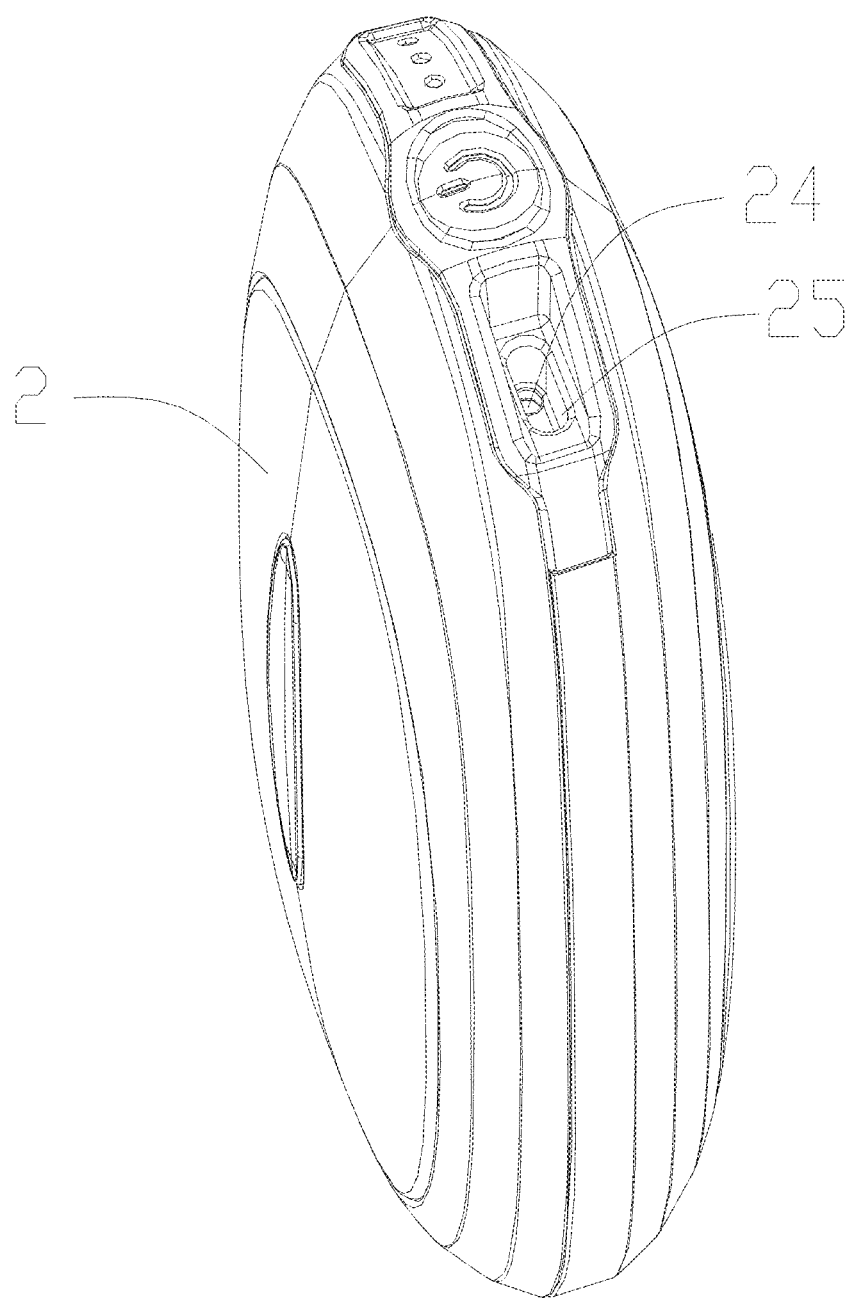
FIG. 9 is a three-dimensional diagram of a hand warmer unit according to the present disclosure.
Figure 10:
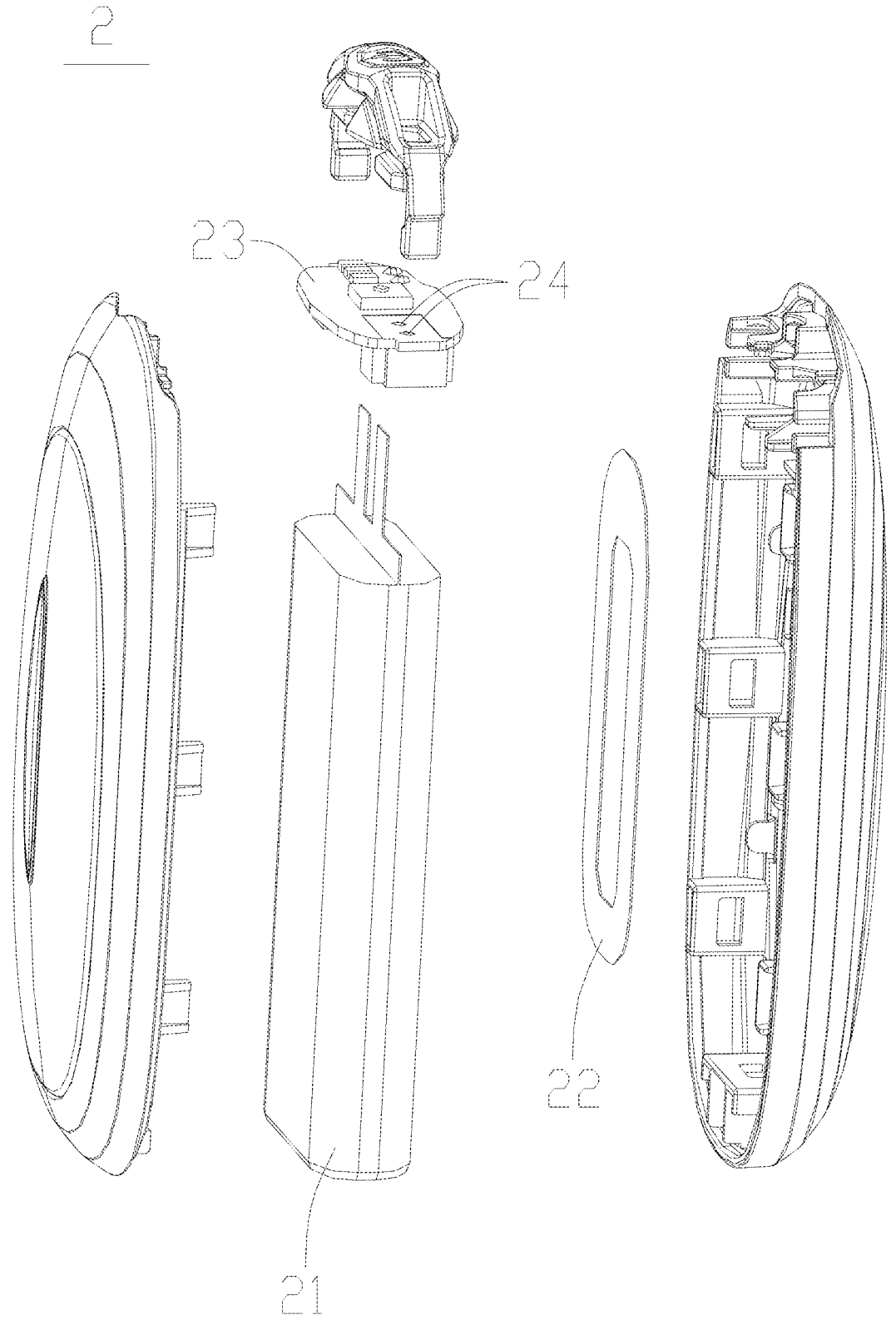
FIG. 10 is an exploded view of a hand warmer unit according to the present disclosure.
Figure 11:
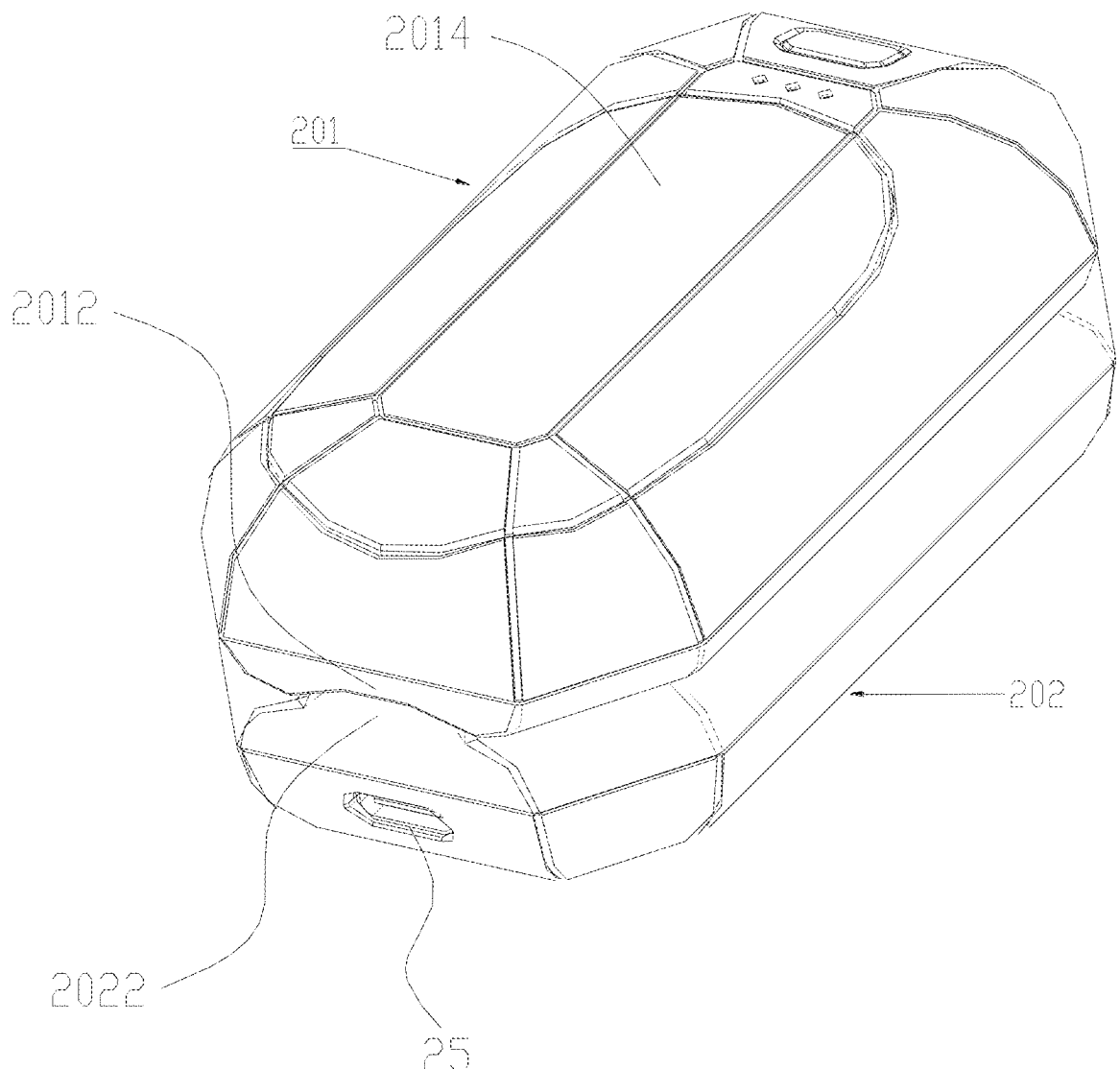
FIG. 11 is a schematic diagram of integrally assembling a first hand warmer and a second hand warmer according to the present disclosure.
Figure 12:
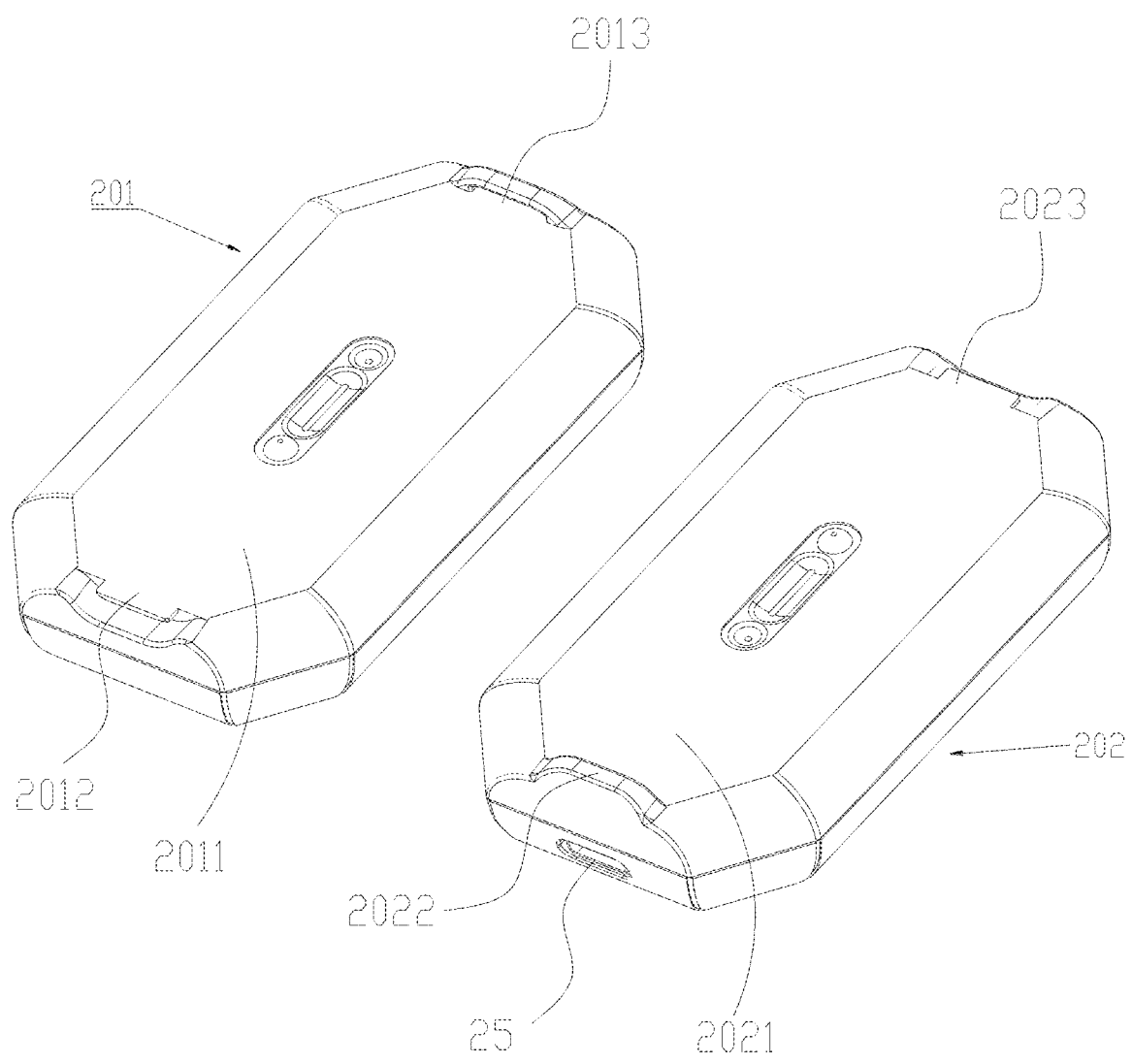
FIG. 12 is an exploded diagram of a first hand warmer and a second hand warmer according to the present disclosure.

Referring to FIG. 11 to FIG. 12, in an embodiment, there are two hand warmer units 2: a first hand warmer 201 and a second hand warmer 202. Correspondingly, there are two placement chambers 3.

In an embodiment, the first hand warmer 201 is detachably connected to the second hand warmer 202, so that the first hand warmer 201 and the second hand warmer 202 are combined into a whole. When a user needs to warm both hands/multiple body parts at the same time, the first hand warmer 201 can be separated from the second hand warmer 202, so that the first hand warmer 201 and the second hand warmer 202 can be used for warming both hands/multiple different body parts separately. When a user needs to warm one hand/one body part, the first hand warmer 201 and the second hand warmer 202 can be combined into a whole to enlarge a warming area of the hand warmer for one hand/one body part, thus enhancing the warming effect. Moreover, when a user needs to carry or store the hand warmer, the user can selectively carry and store the first hand warmer 201 and the second hand warmer 202 separately according to an actual situation, or selectively combine the first hand warmer 201 with the second hand warmer 202 into a whole for carrying and storage, to meet the needs of the user in multiple scenarios, which greatly improves the user experience.

Specifically, the first hand warmer 201 includes a first outer surface 2014 and a first connecting surface 2011 opposite to the first outer surface 2014; a first connecting portion is arranged on the first connecting surface 2011; the second hand warmer 202 includes a second outer surface and a second connecting surface 2021 opposite to the second outer surface; and a second connecting portion is arranged on the second connecting surface 2021; the first connecting portion is connected to the second connecting portion in one of the following manners: a buckle, a hook and loop fastener, and magnetic suction of a plurality of magnetic suction assemblies, so that the first connecting inner surface is connected to the second connecting inner surface; and the first hand warmer 201 and the second hand warmer 202 are combined into a whole.

In an embodiment, the first connecting portion includes a first clamping slot 2013 and a first buckle 2012; the first clamping slot 2013 and the first buckle 2012 are respectively located at two ends of the hand warmer unit 2; the second connecting portion includes a second clamping slot 2022 and a second buckle 2023; the first buckle 2012 is clamped with the second clamping slot 2022 when the first hand warmer 201 and second hand warmer 202 are assembled together; and the second buckle 2023 is clamped with the first clamping slot 2013 when the first hand warmer 201 and second hand warmer 202 are assembled together. In this way, the buckle structures at the two ends can assemble the first hand warmer 201 with the second hand warmer 202 stably together. Of course, in other embodiments, the first connecting portion may include two clamping slots, and the second connecting portion may include two buckles adapted to the clamping slots. Alternatively, both the first connecting portion and the second connecting portion can be hook and loop fasteners, magnets, or the like, and the first hand warmer 201 and the second hand warmer 202 can be detachably connected to each other.

In an embodiment, the hand warmer unit 2 is further provided with a second charging interface 25 for an external power cable. The second charging interface 25 is used for being externally connected to a power supply. After the power supply is connected, the second battery 21 can be charged through the second circuit board 23. In order to increase the charging speed when the charging case 1 has low battery, both the charging case 1 and the hand warmer unit 2 can be charged separately through a power cable. When the hand warmer unit 2 is charged using the second charging interface 25, the power of the charging case 1 will not be consumed, so that when a user goes out, the charging case 1 can keep sufficient power for use. Specifically, both the first charging interface 136 and the second charging interface 25 can be Type-C interfaces, Micro USB interfaces, Lightning interfaces, direct current interfaces, and the like.

In an embodiment, the capacity of the first battery is greater than the capacity of the second battery, such as the capacity of the first battery 18 is at least twice that of the second battery 21, so that the charging case 1 can simultaneously fully charge at least two hand warmer units 2. Of course, in other embodiments, the capacity of the first battery 18 may be at least three times, four times, etc. greater than the capacity of the second battery 21, so that the charging case 1 can simultaneously charge two hand warmer units 2 at least twice, making it convenient for a user to use the charging case when the user goes out.

In some embodiments, the case body 10 of the portable hand warmer charging case includes an opening 101, the hand warmer unit 2 is put into or inserted into the placement chamber 10 from the opening 101. In present embodiment, the opening 101 is unsealed, i.e., it is open without a cover, such case body 10 with unsealed opening 101 is more convenient for use, and after use, it can be stored to maintain clean.

Figure 16:
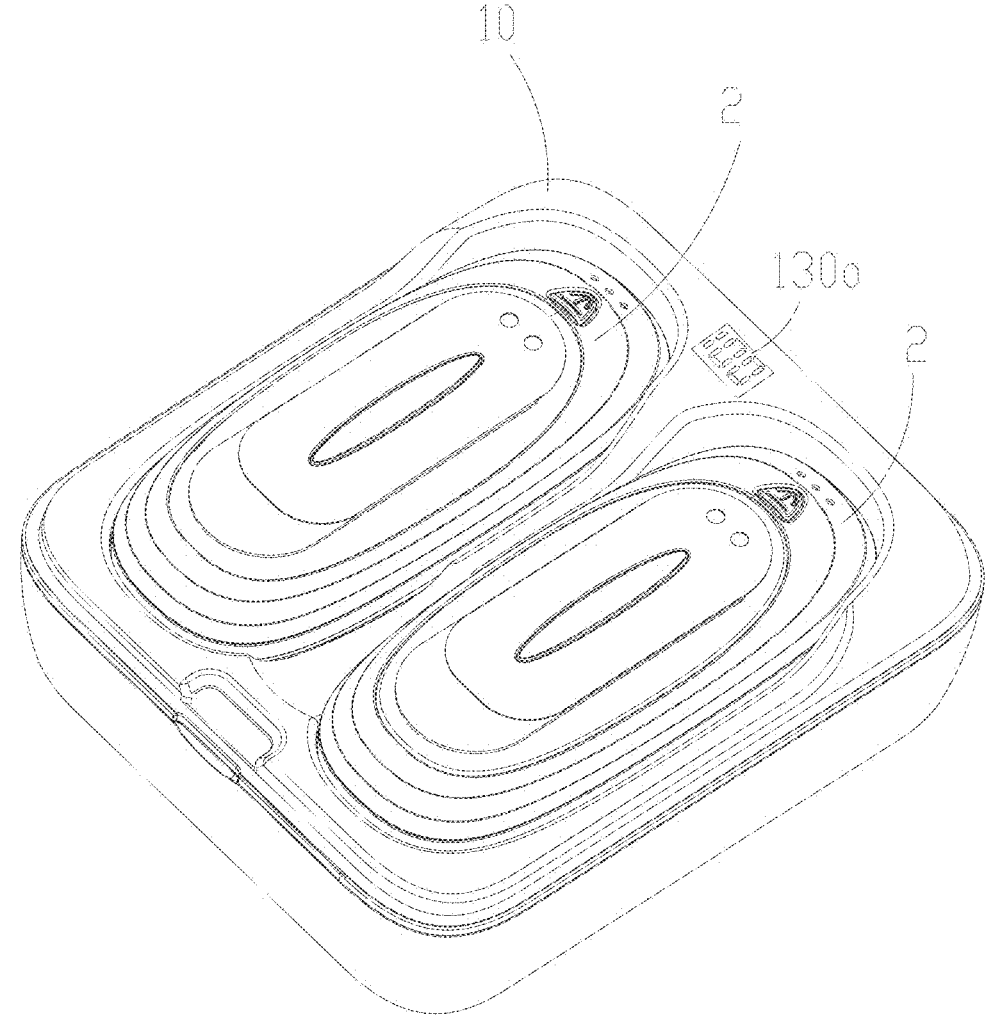
FIG. 16 is a schematic diagram of a portable hand warmer charging case and hand warmer unit in charging state according to another embodiment of the present disclosure.
Figure 17:
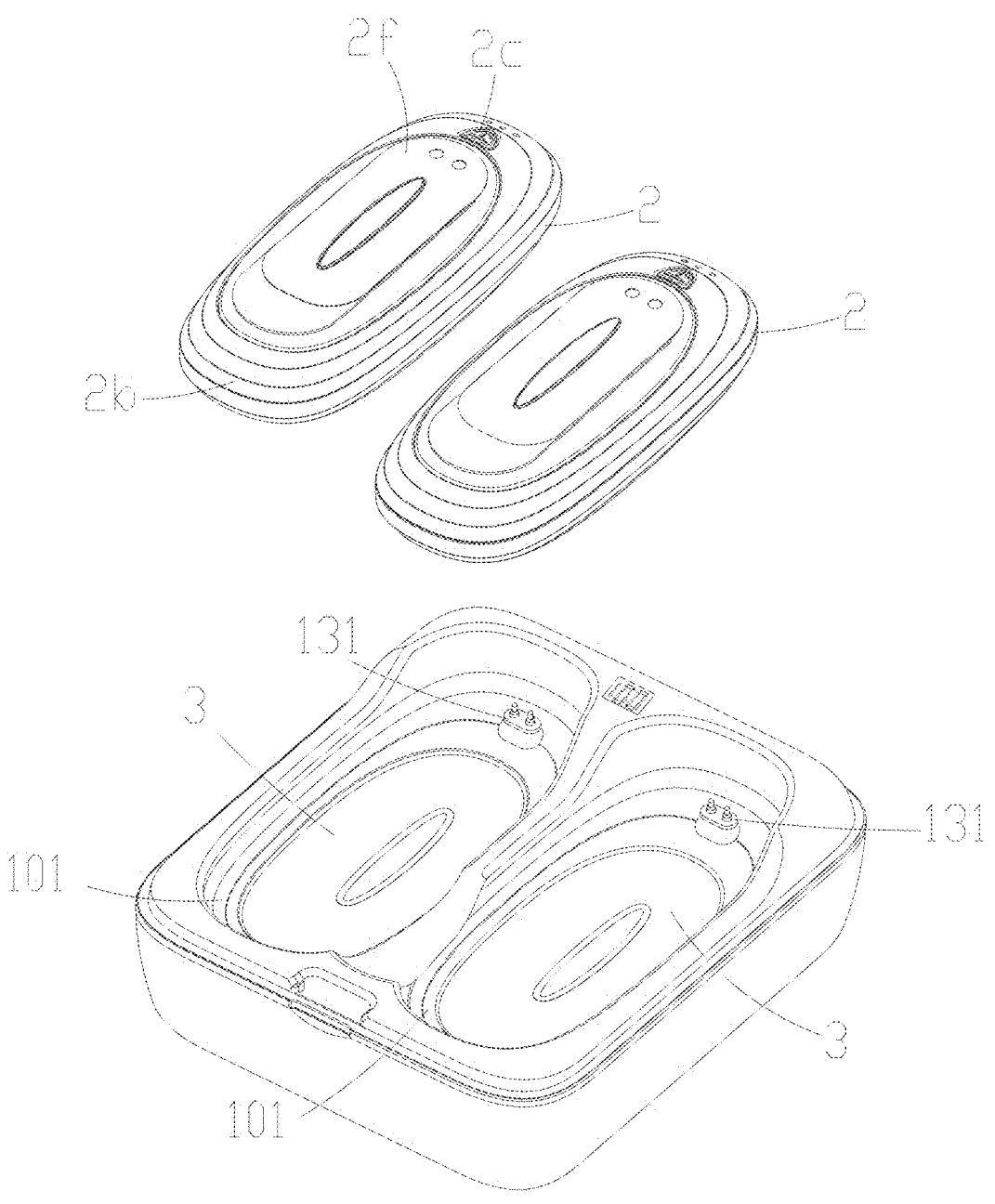
FIG. 17 shows the hand warmer unit taken out of the charging case of FIG. 16.
Figure 18:
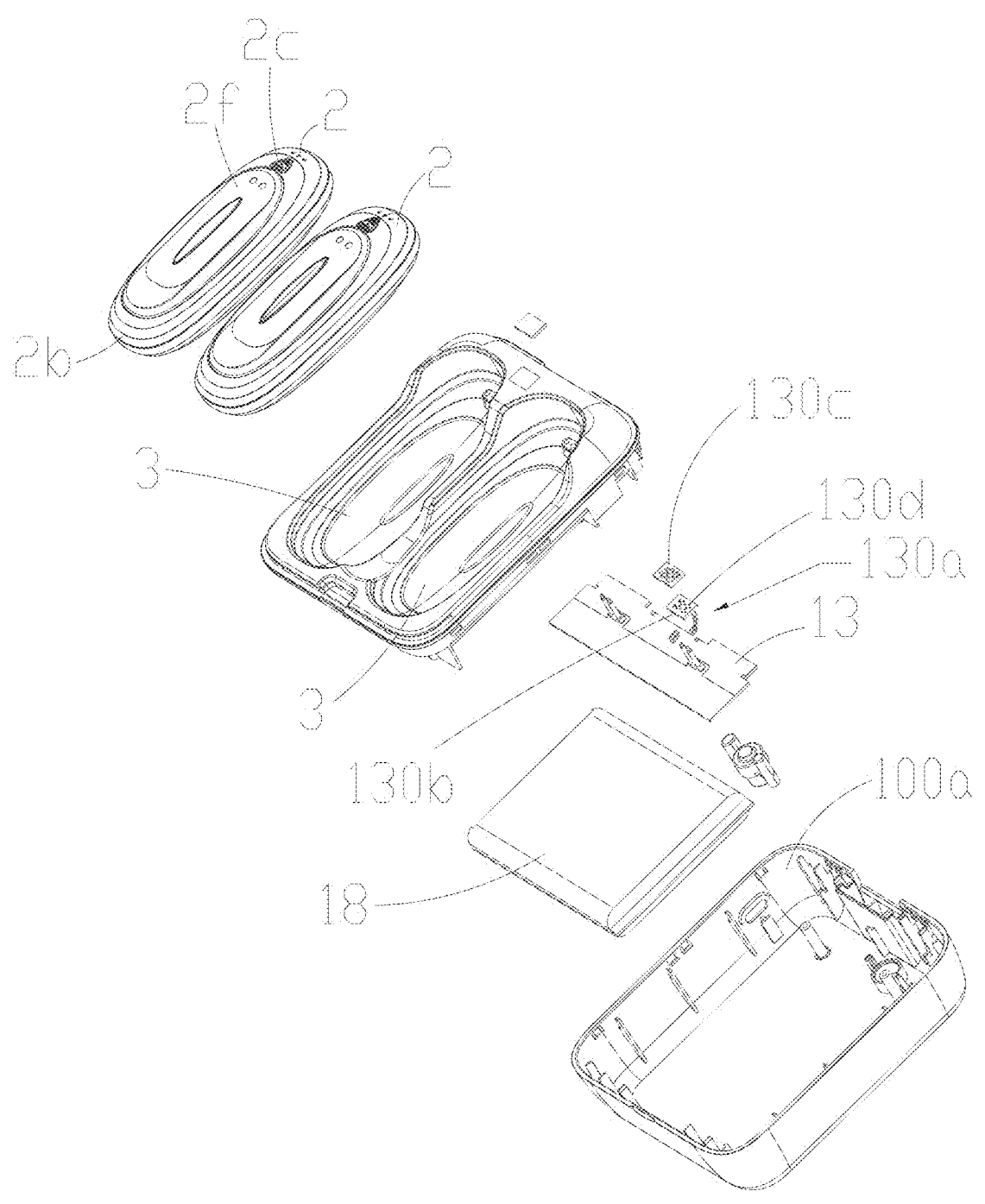
FIG. 18 is an exploded view of FIG. 17.

In particular, referring to FIGS. 16-18, in this embodiment, the opening 101 faces upwards, the conductive probe 131 faces a direction of the opening 101 to adapt for an inserting direction of the hand warmer unit 2, the hand warmer unit 2 has the second charging unit 24 to adapt for the conductive probe 131. The case body 10 is provided with an indicator unit 130a configured to indicate a battery level state of the first battery 18 and/or a charging state of the hand warmer unit 2, the indicator unit 130a is displayed facing an upper surface of the case body 10. The placement chamber 3 is configured for the hand warmer unit 2 being placed flat in the placement chamber 3, after the hand warmer unit 2 is placed in the placement chamber 3, an upper surface 2f of the hand warmer unit 2 faces upwards, and is exposed at the opening 101.

The indicator unit 130a is electrically connected to the first circuit board 13, and the indicator unit 130a is a display screen, and display number representing the charging state, for example, when 100 is displayed, it represents the charging state is finished 100%. It can be understood that the display screen 130a may include a light-emitting light board 130b electrically connected to the first circuit board 13 and a display cover 130c arranged on the light-emitting light board 130b. The light-emitting light board 100b has multiple light-emitting elements 130d, and the first circuit board 13 controls the digital display on the display screen 130a by controlling the light emission or turn off of the multiple light-emitting elements 130d. The upper surface 2f of the hand warmer unit 2 can have switch or display elements 2c, such switch element can control the hand warmer unit 2, and such display element can display the state of the hand warmer unit 2, such as battery level state or abnormal alarm information.

In the above embodiment, the number of the placement chamber 3 is two, the number of the openings 101 are two, and the two placement chambers 3 are parallel with each other, the two openings 101 are parallel with each other and are in communication with each other, such that two hand warmer units 2 can be in charging state at a same time.

In FIG. 18, it shows the charging case substantially includes a housing 100a, the first circuit board 13, the first battery 18 and the placement chambers 3, the placement chambers 3 are integrally formed into one piece, and the one piece served as the upper shell of the case body 10, the first circuit board 13 and the first battery 18 are mounted in the housing 100a, these can be the same as other embodiments.

Figure 19:
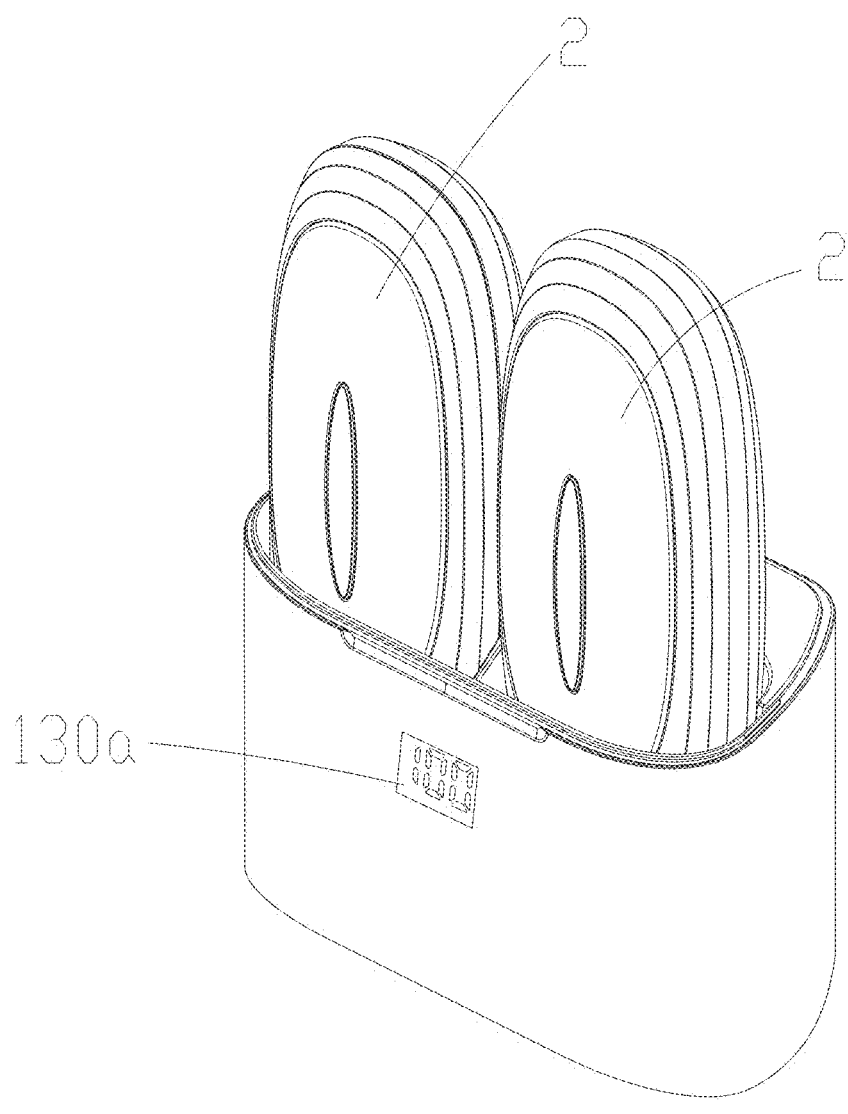
FIG. 19 is a schematic diagram of a portable hand warmer charging case and hand warmer unit in charging state according to further another embodiment of the present disclosure.
Figure 20:
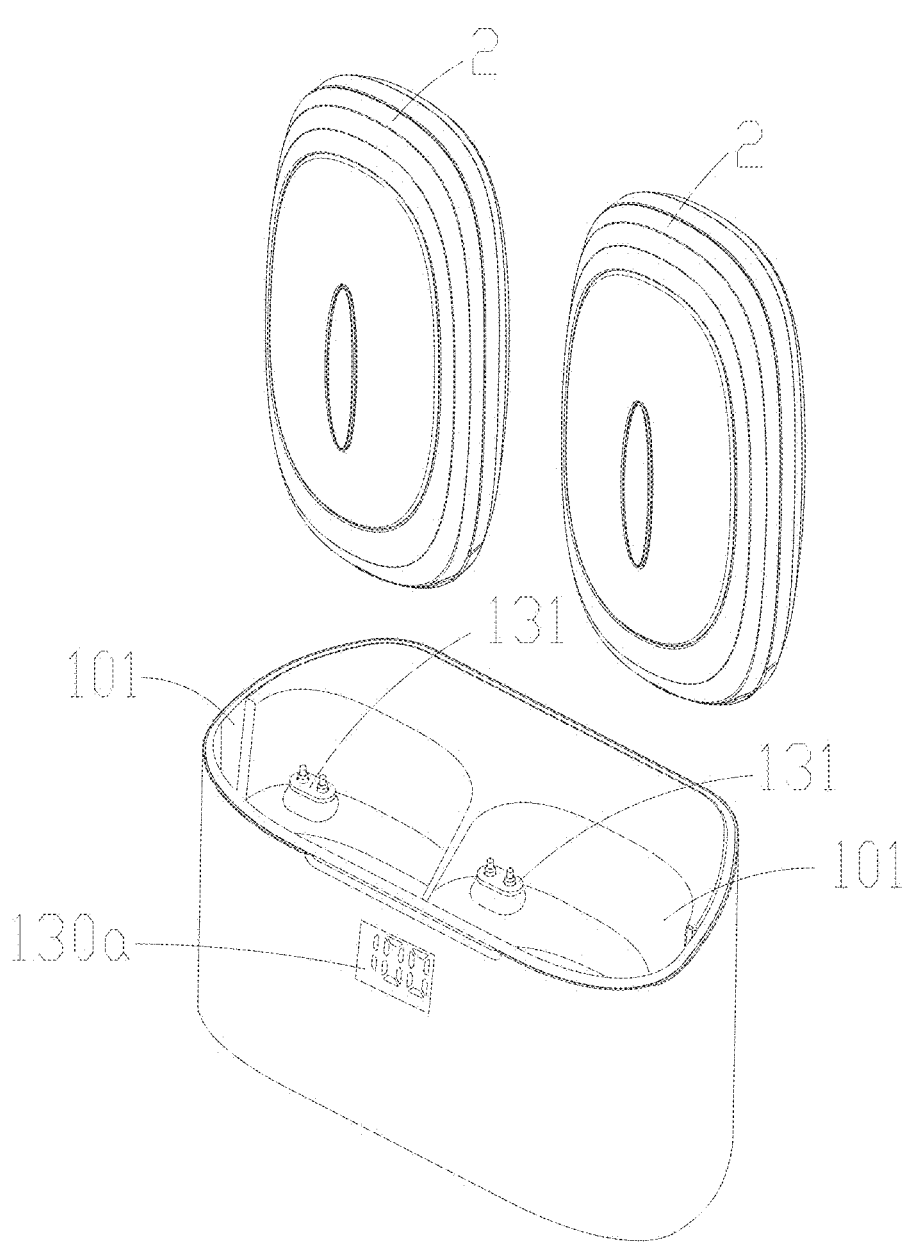
FIG. 20 shows the hand warmer unit taken out of the charging case of FIG. 19.
Figure 21:
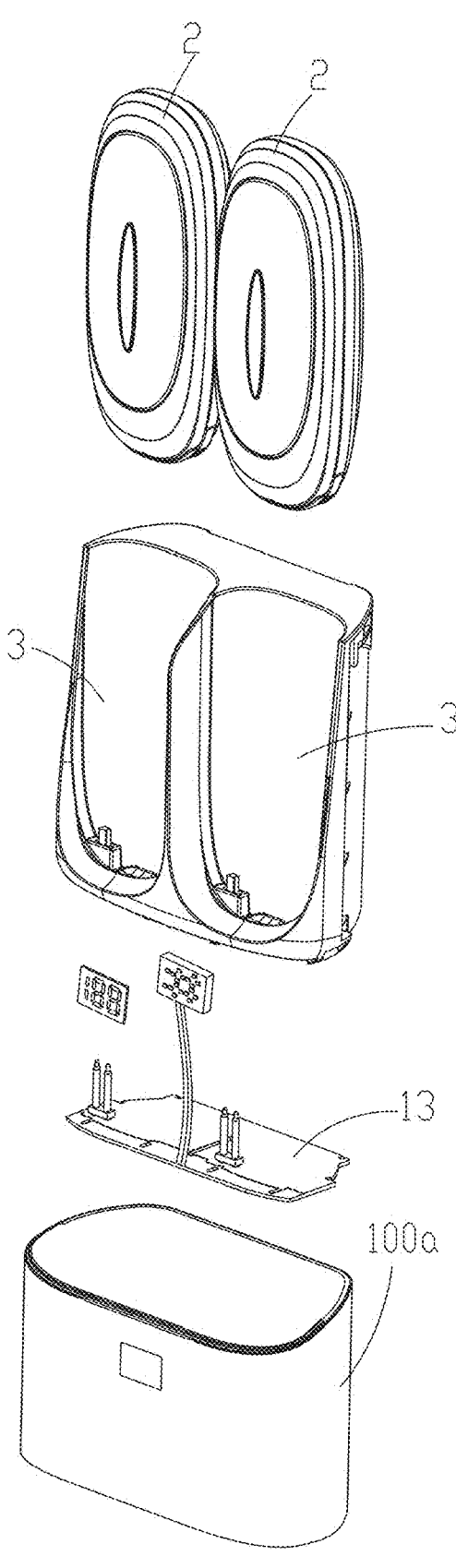
FIG. 21 is an exploded view of FIG. 20.

Referring to FIGS. 19-21, in this embodiment, the opening 101 faces upwards, the case body 10 is provided with an indicator unit 130a configured to indicate a battery level state of the first battery 18 and/or a charging state of the hand warmer unit 2, the indicator unit 130a is displayed facing a side surface of the case body 10. The hand warmer unit 2 comprises an upper surface 2f and an end surface 2b perpendicular to the upper surface 2f, and the placement chamber 3 is configured for the hand warmer unit 2 being vertically inserted into the placement chamber 3, after the hand warmer unit 2 is placed in the placement chamber 3, the end surface of the hand warmer unit 2 faces upwards, and a part of the upper surface 2f is exposed at the opening 101.

In the above embodiment, the number of the placement chamber 3 is two, the number of the openings 101 are two, and the two placement chambers 3 are parallel with each other, the two openings 101 are parallel with each other and are in communication with each other, such that two hand warmer units 2 can be in charging state at a same time.

Referring to FIGS. 22-24, in this embodiment, the opening 101 faces a side surface of the case body 10, the case body 10 is provided with an indicator unit 130a configured to indicate a battery level state of the first battery 18 and/or a charging state of the hand warmer unit 2, the indicator unit 130a is displayed facing the side surface of the case body 10. In this embodiment, the placement chamber 3 is configured for the hand warmer unit 2 being placed to the placement chamber 3 from one side of the case body 10, and after the hand warmer unit 2 is placed in the placement chamber 3, an upper surface of the hand warmer unit 2 faces the side surface of the case body 10, and is exposed at the opening 101.

In the above embodiment, the number of the placement chamber 3 is two, the number of the openings 101 are two, and the two placement chambers 3 are opposite to each other, the two openings 101 are opposite to each other, two hand warmer units 2 can be inserted from opposite side at a same time.

Referring to FIGS. 25-27, in this embodiment, the placement chamber 3 is a groove with a certain depth, which only has an opening 101 at one end to expose the outside, the opening 101 faces a side surface of the case body, the case body 10 is provided with an indicator unit 130a configured to indicate a battery level state of the first battery 18 and/or a charging state of the hand warmer unit 2, the indicator unit 130a is displayed facing the side surface of the case body 10. The hand warmer unit 2 comprises an upper surface 2f and an end surface 2b perpendicular to the upper surface 2f, after the hand warmer unit 2 is placed in the placement chamber 3, the end surface 2b of hand warmer unit 2 is exposed at the opening 101, and the upper surface 2f is not exposed at the opening 101.

In the above embodiment, the number of the placement chamber 3 is two, the number of the openings 101 are two, and the two placement chambers 3 are parallel with each other, the two openings 101 are parallel with each other and in communication with each other, such that two hand warmer units 2 can be in charging state at a same time.

Referring to FIGS. 28-29, in another embodiment, the case body 10 of the portable hand warmer charging case includes a main body 11 and a cover body 12a connected to the main body 11 to form the placement chamber 3. The main body 11 includes the above mentioned housing 100a, the first circuit board 13, the first battery 18 and the placement chamber 3. The cover body 12a is transparent, so that the relevant functions, battery status, or abnormal alarm information of the hand warmer unit 2 can be observed through the transparent cover body 12a.

Referring to FIGS. 30-31, in further another embodiment, it is a portable hand warmer charging device 10d without a cover, but also has the housing 100a, the first circuit board 13, the first battery 18, and the portable hand warmer charging device 10d has a placement portion 3a, the placement portion 3a is only a flat portion, not a chamber illustrated in above embodiments, when the hand warmer unit 2 is placed thereon, it can be charged through contact or through wireless manner, in this embodiment, wireless charging is used as a schematic illustration.

Referring to FIGS. 31 and 32, a wireless charging assembly 3b having a wireless charging coil 3c is arranged under the placement portion 3a, and is electrically connected to the first circuit board 13. The wireless charging assembly 3b further includes a first magnetic member 3d, the first magnetic member 3d can be circular magnetic member, in detail, the first magnetic member 3d surrounds the wireless charging coil 3c. The hand warmer unit 2 has a second magnetic member 2a and a wireless charging coil 2b arranged therein, the second magnetic member 2a corresponds to the first magnetic member 3d. The hand warmer unit 2 can be attached to the placement portion 3a by abstraction of the first magnetic member 3d and the second magnetic member 2a, and after the hand warmer unit 2 is abstracted to the placement portion 3a, the wireless charging coil 3c can correspond to the wireless charging coil 2b to charge the hand warmer unit 2. Furthermore, in present embodiment, each of the two hand warmer units 2 has the second magnetic member 2a, the two warmer units 2 can be combined as a whole by attraction between the second magnetic members 2a, in this way, the second magnetic member 2a is not only used to attach the hand warmer unit 2 to the placement portion 3a of the portable hand warmer charging device 10d when in charging, but also used to connect the two warmer units 2 to be a combination. In this way, a design cost can be reduced, and a user experience can be better. In present embodiment, the two hand warmer units 2 are combined up and down by bottom surfaces attracted together, and upper surface 2f can face outside, the upper surface 2f can warm hand, the combination is more convenient to carry, and can increase the hand warming temperature.

Referring again to FIG. 28 or 30, the portable hand warmer charging case or the portable hand warmer charging device 10d further includes one or more charging interfere 10a which is electrically connected to the first circuit board 13, and is configured for charging other devices which are not the hand warmer units 2. The charging interface 10a can be a type-C female socket interface, a USB type-A female socket interface, etc. This embodiment mainly illustrates the charging interface 10a as a type-C female socket interface. By setting the charging interface 10a, the hand warmer charging device 10d can also charge the hand warmer unit 2 through an external data cable, or charge other electronic devices such as mobile phones through an external data cable, making it versatile and providing a better user experience.

It should be noted that all directional indications (such as up, down, left, right, front, back . . . ) in the embodiments of the present disclosure are only used to explain a relative positional relationship between components, motion situations, etc. at a certain specific attitude (as shown in the figures). If the specific attitude changes, the directional indication also correspondingly changes.

In addition, the descriptions of "first", "second", etc. in the present disclosure are only used for descriptive purposes, and cannot be understood as indicating or implying its relative importance or implicitly indicating the number of technical features indicated. Therefore, features defined by "first" and "second" can explicitly instruct or impliedly include at least one feature. In addition, "and/or" in the entire text includes three solutions. A and/or B is taken as an example, including technical solution A, technical solution B, and technical solutions that both A and B satisfy. In addition, the technical solutions between the various embodiments can be combined with each other, but it needs be based on what can be achieved by those of ordinary skill in the art. When the combination of the technical solutions is contradictory or cannot be achieved, it should be considered that such a combination of the technical solutions does not exist, and is not within the scope of protection claimed by the present disclosure.

The above descriptions are only preferred embodiments of the present disclosure, and are not intended to limit the patent scope of the present disclosure. Any equivalent structural transformation made by using the content of the specification and the drawings of the present disclosure under the invention idea of the present disclosure, directly or indirectly applied to other related technical fields, shall all be included in the scope of patent protection of the present disclosure.

What is claimed is:

1. A hand warmer assembly, comprising at least one hand warmer unit and a charging case, wherein the charging case comprises a case body, the case body comprises a placement chamber configured to place the hand warmer unit for charging, and the case body further comprises an opening, the hand warmer unit is put into the placement chamber from the opening;

the case body further comprises a first circuit board, and a first charging unit; the first charging unit is electrically connected to the first circuit board;

the hand warmer unit is provided with a second circuit board, a heating element, a second battery, and a second charging unit; the heating element, the second battery, and the second charging unit are all electrically connected to the second circuit board;

when the hand warmer unit is placed in the placement chamber, the second charging unit is close to or in contact with the first charging unit; the first charging unit is configured to output electrical energy, which is output by the first circuit board, to the second charging unit; and the second charging unit charges, via the second circuit board, the second battery with the electrical energy output by the first charging unit, and the hand warmer unit is capable of warming hand through working of the heating element.

2. The hand warmer assembly according to claim 1, wherein the first charging unit is a conductive probe; the conductive probe is arranged at the bottom of the placement chamber; the second charging unit is a charging contact; the charging contact is located at a corresponding position of the hand warmer unit, and the charging contact is in contact with the conductive probe when the hand warmer unit is placed in the placement chamber.

3. The hand warmer assembly according to claim 1, further comprising another hand warmer unit and another placement chamber; and the two hand warmer units are detachably connected to each other, and the two hand warmer units are charged through the two placement chambers.

4. The hand warmer assembly according to claim 3, wherein the first hand warmer comprises a first outer surface and a first connecting surface opposite to the first outer surface; a first connecting portion is arranged on the first connecting surface;

the second hand warmer comprises a second outer surface and a second connecting surface opposite to the second outer surface; a second connecting portion is arranged on the second connecting surface;

the first connecting portion is connected to the second connecting portion in one of the following manners: a buckle, a hook and loop fastener, and magnetic suction of a plurality of magnetic suction assemblies, so that the first connecting surface is connected to the second connecting surface; and the first hand warmer and the second hand warmer are combined into a whole.

5. The hand warmer assembly according to claim 1, wherein the hand warmer unit is further provided with another charging interface configured to be externally connected with a power cable.

6. A portable hand warmer assembly, comprising at least one hand warmer unit and a portable charging device, and the portable charging device comprises at least one placement portion configured for placing the at least one hand warmer unit;

the portable charging device comprise a first charging unit, the at least one hand warmer unit comprises a second charging unit, after the at least one hand warmer unit is placed at the placement portion, the first charging unit is capable of charging the second charging unit;

wherein the at least one placement portion is inwardly concave, and the at least one placement portion is exposed without a cover body, the at least one hand warmer unit is placed at the at least one placement portion in a manner that less than a half of length of the at least one hand warmer unit is inserted in the at least one placement portion and more than a half of the length of the at least one hand warmer unit is exposed outside the at least one placement portion, and the at least one hand warmer unit comprises an upper surface along the length direction, with the upper surface being capable of warming hand.

7. The portable hand warmer assembly according to claim 6, wherein the first charging unit charges the second charging unit through contact or through wireless manner.

8. The portable hand warmer assembly according to claim 6, wherein the upper surface of the at least one hand warmer unit has a switch or display elements.

9. The portable hand warmer assembly according to claim 6, wherein portable charging device has a display screen thereon.

10. The portable hand warmer assembly according to claim 6, wherein the at least one placement portion comprises two placement portions, and the two placement portions are parallel with each other.

11. The portable hand warmer assembly according to claim 6, wherein the first charging unit is a conductive probe; the conductive probe is arranged at the bottom of the placement chamber; the second charging unit is a charging contact; the charging contact is located at a corresponding position of the hand warmer unit, and the charging contact is in contact with the conductive probe when the hand warmer unit is placed in the placement chamber.

12. A portable hand warmer assembly, comprising at least one hand warmer unit and a portable charging device, and the portable charging device comprises a placement portion configured for placing the at least one hand warmer unit;

the portable charging device comprise a first charging unit, the at least one hand warmer unit comprises a second charging unit, after the at least one hand warmer unit is placed at the placement portion, the first charging unit is capable of charging the second charging unit;

wherein the placement portion is a flat portion, and a wireless charging assembly is arranged under the placement portion, the wireless charging assembly comprises a first wireless charging coil, and a first magnetic member surrounding the first wireless charging coil, the at least one hand warmer unit comprises a second magnetic member and a second wireless charging coil arranged therein, the at least one hand warmer unit is capable of being attached to the placement portion by abstraction of the first magnetic member and the second magnetic member, and after the at least one hand warmer unit is abstracted to the placement portion, the first wireless charging coil corresponds to the second wireless charging coil to charge the at least one hand warmer unit.

\* \* \* \* \*